(12) United States Patent
Saha et al.

(10) Patent No.: US 11,739,320 B2
(45) Date of Patent: Aug. 29, 2023

(54) GENE CORRECTION OF POMPE DISEASE AND OTHER AUTOSOMAL RECESSIVE DISORDERS VIA RNA-GUIDED NUCLEASES

(71) Applicant: Wisconsin Alumni Research Foundation, Madison, WI (US)

(72) Inventors: Krishanu Saha, Middleton, WI (US); Jared Matthew Carlson-Stevermer, Burlingame, CA (US); Lucille Katherine Kohlenberg, Elm Grove, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 769 days.

(21) Appl. No.: 16/674,448

(22) Filed: Nov. 5, 2019

(65) Prior Publication Data

US 2020/0140858 A1 May 7, 2020

Related U.S. Application Data

(60) Provisional application No. 62/755,980, filed on Nov. 5, 2018.

(51) Int. Cl.

| | | |
|---|---|---|
| *C12N 15/11* | (2006.01) | |
| *C12N 9/22* | (2006.01) | |
| *A61P 3/00* | (2006.01) | |
| *A61K 35/545* | (2015.01) | |
| *C12N 15/86* | (2006.01) | |
| *A61K 31/7088* | (2006.01) | |

(52) U.S. Cl.
CPC .......... *C12N 15/11* (2013.01); *A61K 31/7088* (2013.01); *A61K 35/545* (2013.01); *A61P 3/00* (2018.01); *C12N 9/22* (2013.01); *C12N 15/86* (2013.01); *C12N 2310/20* (2017.05); *C12N 2310/351* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 8,889,418 B2 | 11/2014 | Zhang et al. | |
| 9,856,497 B2 | 1/2018 | Qi et al. | |
| 9,868,962 B2 | 1/2018 | May et al. | |
| 10,377,998 B2 | 8/2019 | Zhang et al. | |
| 10,450,584 B2 | 10/2019 | Barrangou et al. | |
| 10,920,221 B2 | 2/2021 | Rinn et al. | |
| 2014/0357523 A1 | 12/2014 | Zeiner et al. | |
| 2015/0283265 A1 | 10/2015 | Peyman | |
| 2017/0081650 A1 | 3/2017 | Joung et al. | |
| 2017/0152508 A1 | 7/2017 | Joung et al. | |
| 2021/0139891 A1 | 5/2021 | Carlson-Stevermer et al. | |

FOREIGN PATENT DOCUMENTS

| | | |
|---|---|---|
| CN | 102858985 A | 1/2013 |
| CN | 105188767 A | 12/2015 |
| CN | 111246846 A | 6/2020 |
| UA | 20180362971 A1 | 12/2018 |
| WO | 2016014409 A1 | 1/2016 |
| WO | 2016183402 A2 | 11/2016 |

OTHER PUBLICATIONS

Kohler, et al. (2018) "Pompe Disease: From Basic Science to Therapy", Neurotherapeutics, 15: 928-42. (Year: 2018).*
Bao et al.; "Multifunctional Nanoparticles for Drug Delivery and Molecular Imaging"; Annu. Rev. Biomed. Eng.; 15; pp. 253-282; (2013).
Brinkman et al.; "Easy Quantitative Assessment of Genome Editing by Sequence Trace Decomposition"; Nucleic Acids Research; 8 pages, (2014), downloaded from https://academic.oup.com/nar/article-abstract/42/22/e168/2411890, by University of Wisconsin-Madison on Jul. 5, 2018.
Carlson-Stevermer et al.; "Assembly of CRISPR Ribonucleoproteins With Biotinylated Oligonucleotides Via an RNA Aptamer for Precise Gene Editing"; Nature Communications; 8(1); 13 pages; (2017).
Carlson-Stevermer et al.; "High-Content Analysis of CRISPR-CasG Gene-Edited Human Embryonic Stem Cells"; Stem Cell Reports; 6; pp. 109-120; (2016).
Chu et al.; "Increasing the Efficiency of Homology-Directed Repair for CRISPR-Cas9-Induced Precise Gene Editing in Mammalian Cells"; Nature Biotechnology; 33(5); pp. 543-550; (2015).
Darmostuk et al.; "Current Approaches in SELEX: An Update to Aptamer Selection Technology"; Biotechnology Advances; 33; pp. 1141-1161; (2015).
Davis et al.; "Small Molecule-Triggered Cas9 Protein With Improved Genome-Editing Specificity"; Nature Chemical Biology; vol. 11, pp. 316-318; (2015).
De Ravin et al.; "CRISPR-Cas9 Gene Repair of Hematopoietic Stem Cells From Patients with X-Linked Chronic Granulomatous Disease"; Sci. Transl. Med.; 9; eaah3480; 10 pages; (2017).
Dever el al.; "CRISPR/Cas9 Beta-globin Gene Targeting in Human Haematopoietic Stem Cells"; Nature; vol. 539; 384, 19 pages; (2016).

(Continued)

*Primary Examiner* — Robert M Kelly
(74) *Attorney, Agent, or Firm* — Cantor Colburn LLP

(57) ABSTRACT

Described herein are guide RNAs and modified guide RNAs suitable for biallelic correction of Pompe disease. Also included are methods of modifying a target gene in a patient or in a patient-derived cell, wherein the patient has an autosomal recessive disorder with compound heterozygous mutations, the methods including delivering a first modified guide RNA, a second modified guide RNA, a Cas9 polypeptide, a biotin-binding molecule, a first biotinylated donor polynucleotide, and a second biotinylated donor polynucleotide. The first modified guide RNA and the first biotinylated donor polynucleotide correct a first diseased allele, and the second modified guide RNA and the second biotinylated donor polynucleotide correct a second diseased allele.

21 Claims, 12 Drawing Sheets
(10 of 12 Drawing Sheet(s) Filed in Color)
Specification includes a Sequence Listing.

(56) References Cited

OTHER PUBLICATIONS

DeWitt et al; "Selection-Free Genome Editing at the Sickle Mutation in Human Adult Hematopoietic Stem/Progenitor Cells"; Sci. Transl. Med.; 8; 360ra134; 9 pages; (2616).
Duda et al; "High-Efficiency Genome Editing Via 2A-Coupled Co-Expression of Fluorescent Proteins and Zinc Finger Nucleases or CRISPR/Cas9 Nickase Pairs"; Nucleic Acids Research; 42(10);; e84; 16 pages: (2014); downloaded from https://academic.oup.com/nar/article-abstract/42/10/e84/2434652 by University of Wisconsin-Madison Libraries on Jul. 5, 2018.
Ellington et al.; "In Vitro Selection of RNA Molecules That Bind Specific Ligands"; Nature; 346; pp. 818-822; (1990).
Eyquem et al.; "Targeting a CAR to the TRAC Locus With CRISPR/Cas9 Enhances Tumour Rejection"; Nature; vol. 543; p. 113; 19 pages; (2017).
Gaj et al.; "Targeted Gene Knock-In By Homology-Directed Genome Editing Using Cas9 Ribonucleoprotein and AAV Donor Delivery"; Nucleic Acids Research; 45(11); e98; 11 pages, Downloaded from https://academic.oup.com/nar/article-abstract/45/11/398/3059660 by University of Wisconsin-Madison on Jul. 5, 2018.
Hemphill et al.; "Optical Control of CRISPR/Cas9 Gene Editing"; J. Am. Chem. Soc.; 137; pp. 5642-5645; (2015).
International Search Report and Written Opinion; International Application No. PCT/US2018/037531; International filing date Jun. 14, 2018; dated Sep. 6, 2018; 18 pages.
Kleinstiver et al.; "High-Fidelity CRISPR-Cas9 Nucleases With No Detectable Genome-Wide Off-Target Effects"; Nature; 529; p. 490; 17 pages; (2016).
Konermann et al.; "Genome-Scale Transcriptional Activation By An Engineered CRISPR-Cas9 Complex"; Nature; vol. 517; p. 583-585; (2015).
Landrum et al.; "ClinVar: Public Archive Of Interpretations of Clinically Relevant Variants"; D862-D868 Nucleic Acids Research; vol. 44, pp. D862-D868; Database issue; (2016).
Le Trong et al.; "Streptavidin and Its Biotin Complex at Atomic Resolution"; Acta Cryst.; D67; pp. 813-821; (2011).
Lee et al.; "Synthetically Modified Guide RNA and Donor DNA are a Versatile Platform for CRISPR-CaS9 Engineering"; ELIFE; 6; 17 pages; (2017).
Leppek et al.; "An Optimized Streptavidin-Binding RNA Aptamer for Purification of Ribonucleoprotein Complexes Identifies Novel ARE-Binding Proteins"; Nucleic Acids Research; vol. 42(2); e13; 15 pages; (2014), downloaded from https://academic.oup.com/nar/article-abstract/42/2/e13/1030103 by University of Wisconsin-Madison Libraries on Jul. 5, 2018.
Li et al.; "Optimization of Genome Engineering Approaches With The CRISPR/Cas9 System"; PLoS One; 9(8): e105779. doi:10.1371/journal.pone.0105779; (2014).
Liang et al.; "Enhanced CRISPR/Cas9-Mediated Precise Genome Editing by Improved Design and Delivery of gRNA, Cas9 Nuclease, and Donor DNA"; Journal of Biotechnology; 241; pp. 136-146; (2017).
Lin et al.; "Enhanced Homology-Directed Human Genome Engineering by Controlled Timing of CRISPR/Cas9 Delivery"; Weigel D, ed. eLife.; 32 pages; (2014);3:e04766. doi:10.7554/eLife.04766.
Lonowski et al.; "Genome Editing Using FACS Enrichment of Nuclease-Expressing Cells and Indel Detection by Amplicon Analysis"; Nature Protocols; 12(3); pp. 581-603; (2017).
Ma et al.; "Efficient Generation of Mice Carrying Homozygous Double-Floxp Alleles Using the Cas9-Avidin/Biotin-Donor DNA System"; Cell Research; 27; pp. 578-581; (2017).
Maruyama et al.; "Increasing the Efficiency of Precise Genome Editing With CRISPR-Cas by Inhibition of Nonhomologous End Joinging" Nature Biotechnology; 33(5); p. 538; 9 pages; (2015).
Merkle et al.; "Efficient CRISPR-Cas9-Mediated Generation of Knockin Human Pluripotent Stem Cells Lacking Undesired Mutations at the Targeted Locus": Cell Reports; 11; pp. 875-883; (2015).
Ming et al.; "Efficient Generation of Mice Carrying Homozygous Double-floxp Alleles Using the Cas9-Avidin/Biotin-Donor DNA System"; Cell Research; 27; pp. 578-581; (2017).

Nishimasu et al.; "Crystal Structure of Cas9 in Complex with Guide RNA and Target DNA"; Cell; 156; pp. 935-949; (2014).
Paquet et al.; "Efficient Introduction of Specific Homozygous and Heterozygous Mutations Using CRISPR/Cas9"; Nature; 533; p. 125; 18 pages; (2016).
Pattanayak et al.; "High-Throughput Profiling of Off-Target DNA Cleavage Reveals RNA-Programmed Cas9 Nuclease Specificity"; Nature Biotechnology; 31(9); pp. 839-845; (2013).
Ran et. al.; "Genome Engineering Using the CRISPR-Cas9 System"; Nature Protocols; 8(11); pp. 2281-2308; (2013).
Richardson et al.; "Enhancing Homology-Directed Genome Editing by Catalytically Active and Inactive CRISPR-Cas9 Using Asymmetric Donor DNA"; Nature Biotechnology; 34(3); pp. 339-345; (2016).
Ruigrok et al.; "Kinetic and Stoichiometric Characterisation of Streptavidin-Binding Apramers"; ChemBioChem; 13; pp. 829-836; (2012).
Sevier et al.; "Formation and Transfer of Disulphide Bonds In Living Cells"; Nature Reviews; Molecular Cell Biology; 3; pp. 836-847; (2002).
Shechner et al, pp. 1-37 of Supplementary Information; Nature Methods 12(7); pp. 664-670, and pp. 1-5 of Online Methods, 2015, which is cited as reference 31 on the IDS filed Aug. 21, 2018; 2015).
Shechner, et al.; "Multiplexable, Locus-Specific Targeting of Long RNAs With CRISPR-Display"; Nature Methods; 12(7); p. 664; 12 pages (2015).
Song et al.; "RS-1 Enhances CRISPR/CaS9- and TALEN-Mediated Knock-In Efficiency"; Nature Communications 7 pages; Article No. 10548; (2016).
Srisawat et al.; "Streptavidin Aptamers: Affinity Tags for the Study of RNAs and Ribonucleoproteins"; RNA; 7; pp. 632-641; (2001).
Steyer et al.; "Scarless Genome Editing of Human Pluripotent Stem Cells Via Transient Puromycin Selection"; Stem Cell Reports; 10; pp. 642-654; (2018).
U.S. NonFinal Office Action dated Sep. 27, 2018; U.S. Appl. No. 16/008,376, filed Jun. 14, 2018, 19 pages.
U.S. NonFinal Office Action, dated Apr. 19, 2019, U.S. Appl. No. 16/008,376, filed Jun. 14, 2018, 21 pages.
Wang et al.; "In Vitro Selection of High-affinity DNA Aptamers for Streptavidin"; Acta Biochim Biophys Sin; 41(4); pp. 335-340; (2009).
Yang et al.; "Optimization of Scarless Human Stem Cell Genome Editing"; Nucleic Acids Research; 41(19); pp. 9049-9061; (2013).
Zetsche et al.; Nature Biotechnology; 33(2), pp. 139-142, Feb. 2015, including p. 109 of Supplementary Information (2015).
Zuris et al.; "Cationic Lipid-Mediated Delivery of Proteins Enables Efficient Protein-Based Genome Editing In Vitro and In Vivo"; Nature Biotechnology; 33(1); pp. 73-80; (2015).
Chen et al.; "Enhanced proofreading governs CRISPR-Cas9 targeting accuracy"; Nature, vol. 550, Issue No. 7676; 2017; doi:10.1038/nature24268; pp. 407-422.
Chew et al.; "A multifunctional AAV-CRISPR-Cas9 and its host response"; Nature Methods, vol. 13, Issue No. 10; 2016; doi:10.1038/nmeth.3993; pp. 868-879.
Hasegawa et al.; "Methods for Improving Aptamer Binding Affinity"; Molecules, vol. 21, Issue No. 4; 2016; doi:10.3390/molecules21040421; pp. 421-435.
Hernandez et al.; "Aptamers as a model for functional evaluation of LNA and 20-amino LNA"; Bioorganic & Medicinal Chemistry Letters, vol. 19, Issue 23; 2007; doi:10.1016/j.bmcl.2009.10.039; pp. 6585-6587.
Hernandez et al.; "Label free optical sensor for Avidin based on single gold nanoparticles functionalized with aptamers"; Journal of Biophotonics, vol. 2, Issue No. 4; 2009; DOI 10.1002/jbio.200910006; pp. 227-231.
Lorenz et al.; "Genomic systematic evolution of ligands by exponential enrichment (Genomic SELEX) for the identification of protein-binding RNAs independent of their expression levels"; Nature Protocols, vol. 1, Issue No. 5; 2006; doi:10.1038/nprot.2006.372; pp. 2204-2212.

(56) References Cited

OTHER PUBLICATIONS

Ma et al.; "Rational Design of Mini-Cas9 for Transcriptional Activation"; ACS Synthetic Biology, vol. 7, Issue No. 4; 2018; DOI: 10.1021/acssynbio.7b00404; pp. 978-985.

Stoltenburg et al.; "FluMag-SELEX as an advantageous method for DNA aptamer selection"; Analytical and Bioanalytical Chemistry, vol. 383, Issue No. 1; 2005; DOI 10.1007/s00216-005-3388-9; pp. 83-91.

Stoltenburg et al.; "SELEX—a (r) evolutionary method to generate high-affinity nucleic acid ligands"; Biomolecular Engineering, vol. 24, Issue No. 4; 2007; doi:10.1016/j.bioeng.2007.06.001; pp. 381-403.

Walker et al.; "The Dual Use of RNA Aptamer Sequences for Affinity Purification and Localization Studies of RNAs and RNA-Protein Complexes"; Methods in Molecular Biology, vol. 714; 2011; pp. 423-444.

Palumbo, C. et al.; "Versatile 3' Functionalization of CRISPR Single Guide RNA"; Chemcbiochem, vol. 21, Issue No. 11; 2020' pp. 1633-1640; doi:10.1002/cbic.201900736.

\* cited by examiner

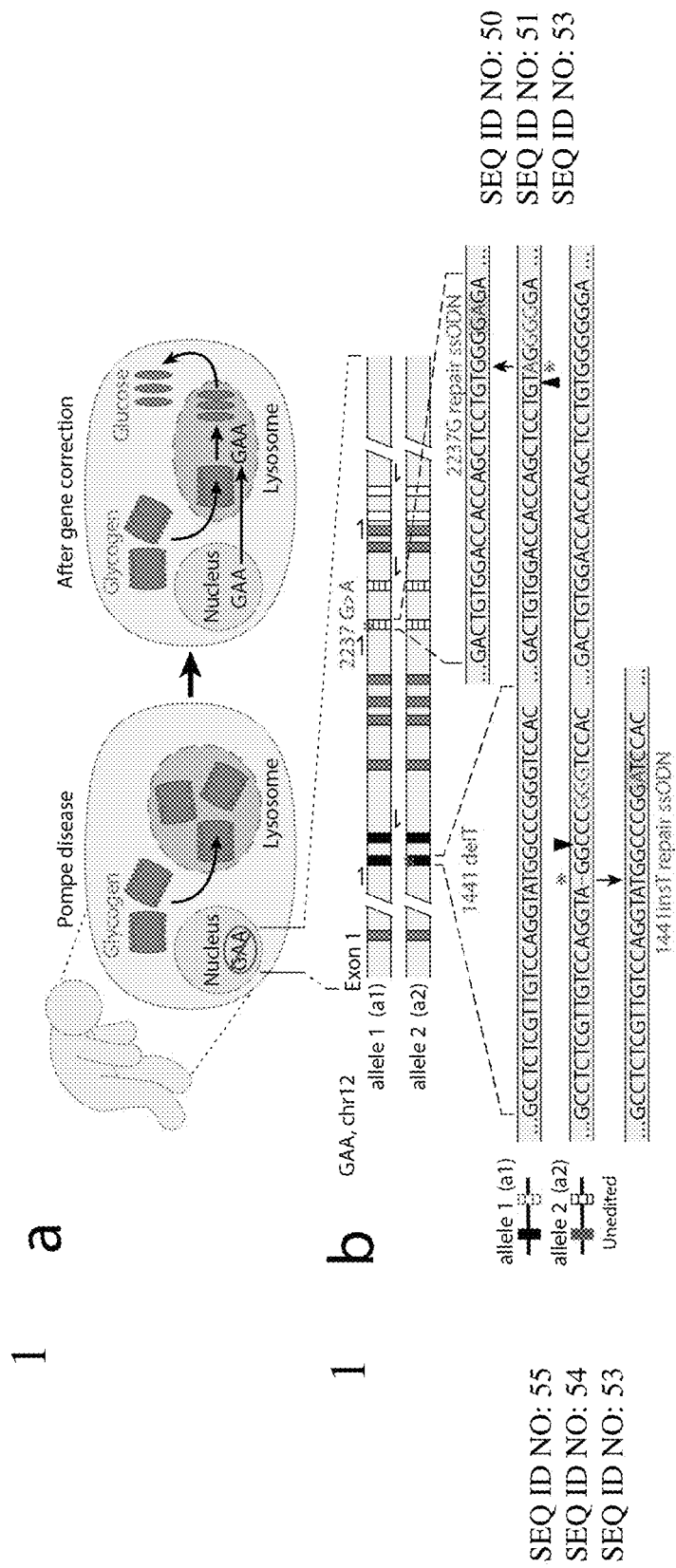
FIG. 1 a and b

GENE CORRECTION OF POMPE DISEASE AND OTHER AUTOSOMAL RECESSIVE DISORDERS VIA RNA-GUIDED NUCLEASES

CROSS-REFERENCE TO RELATED APPLICATIONS

This application claims priority to U.S. Provisional Application 62/755,980 filed on Nov. 5, 2019, which is incorporated herein by reference in its entirety.

STATEMENT REGARDING FEDERALLY SPONSORED RESEARCH & DEVELOPMENT

This invention was made with government support under GM119644 awarded by the National Institutes of Health and CBET1350178 awarded by the National Science Foundation. The government has certain rights in the invention.

FIELD OF THE DISCLOSURE

The present disclosure is related to compositions and methods for the treatment of autosomal recessive diseases.

BACKGROUND

Infantile-onset Pompe disease is an autosomal recessive glycogen storage disorder cause by mutations in the acid-α-glucosidase (GAA) gene that encodes an enzyme that breaks down glycogen within the lysosome (FIG. 1a). Over 400 different GAA mutations have been noted within ClinVar, and detailed case studies indicate a buildup of lysosomic glycogen, leading to clinical complications, most prominently in cardiac and muscle tissues. Left untreated, patients with infantile-onset Pompe disease typically die within the first year of life, and Pompe disease is now frequently included within newborn screening panels. Enzyme replacement therapy (ERT) using recombinant human GAA (rhGAA) is currently the only approved clinical treatment for Pompe disease. However, patients require high levels of enzyme injected biweekly, rendering the treatment expensive and inconvenient. ERT may also be less effective in a subset of patients that are cross-reactive immunologic material (CRIM) negative.

Newer therapies in development for Pompe disease have primarily made use of integrated viral cassettes including transgenes to express GAA from exogenous promoters. Viral particles are injected either directly into muscle or administered systemically and transported to the liver. Direct injection to cardiac or skeletal muscle provided long term recovery of phenotype (10-fold reduction in glycogen content) to transduced cells but did not affect non-transduced cells and required high viral loads ($>10^{10}$ viral genomes/kg). Silencing of the viral transgene, immune response to the viral vector, and insertional oncogenesis are outstanding concerns with these viral gene therapy approaches. Anti-sense oligonucleotides can be introduced to correct splicing in diseased patients that possessed mutations at splicing sites, but would only be beneficial to a subset of potential patients. Finally, autologous cell therapy has been proposed using cells engineered to constitutively overexpress GAA. None of these approaches retain endogenous GAA regulation nor have corrected the underlying GAA mutations.

What is needed are novel strategies for correction of the mutated alleles Pompe disease and other autosomal recessive disorders which could be a promising in vivo somatic gene editing strategy or an alternative strategy to generate gene corrected cells ex vivo for cell therapy.

BRIEF SUMMARY

In one aspect, a modified guide RNA comprises
a crRNA comprising, a single-stranded protospacer sequence and a first complementary strand of a binding region for the Cas9 polypeptide, and
a tracrRNA comprising a second complementary strand of the binding region for the Cas9 polypeptide,
wherein the crRNA or the tracrRNA comprises an aptamer that binds a biotin-binding molecule,
wherein the crRNA and the tracrRNA hybridize through the first and second complementary strands of the binding region for the Cas9 polypeptide,
wherein the single stranded protospacer region comprises

```
                                    (SEQ ID NO: 1)
CTCGTTGTCCAGGTAGGCC, (SEQ ID NO: 2)
TGGACCACCAGCTCCTGTAG, (SEQ ID NO: 60)
GGACCACCAGCTCCTGTAGG, (SEQ ID NO: 61)
GCCCAGGAAGCCGCAGACGT,
or (SEQ ID NO: 62)
CAGAGGAGCTGTGTGTGCAC.
```

In another aspect, a guide RNA comprises
a crRNA comprising, a single-stranded protospacer sequence and a first complementary strand of a binding region for the Cas9 polypeptide, and
a tracrRNA comprising a second complementary strand of the binding region for the Cas9 polypeptide,
wherein the crRNA and the tracrRNA hybridize through the first and second complementary strands of the binding region for the Cas9 polypeptide,
wherein the single stranded protospacer region comprises

```
                                    (SEQ ID NO: 1)
CTCGTTGTCCAGGTAGGCC, (SEQ ID NO: 2)
TGGACCACCAGCTCCTGTAG, (SEQ ID NO: 60)
GGACCACCAGCTCCTGTAGG, (SEQ ID NO: 61)
GCCCAGGAAGCCGCAGACGT,
or (SEQ ID NO: 62)
CAGAGGAGCTGTGTGTGCAC.
```

Also included herein are RNP complexes comprising the guide RNAs and modified guide RNAs, and a Cas9 polypeptide or active fragment thereof.

In another aspect, a method of modifying a target gene in a patient or in a patient-derived cell, wherein the patient has an autosomal recessive disorder with compound heterozygous mutations comprises
delivering to the patient or cell a first modified guide RNA, a second modified guide RNA, a Cas9 polypeptide, a biotin-binding molecule, a first biotinylated donor polynucleotide, and a second biotinylated donor polynucleotide, wherein each modified guide RNA comprises,
   a crRNA comprising, a single-stranded protospacer sequence and a first complementary strand of a binding region for the Cas9 polypeptide, and
   a tracrRNA comprising a second complementary strand of the binding region for the Cas9 polypeptide,
   wherein the crRNA or the tracrRNA comprises an aptamer that binds a biotin-binding molecule,
   wherein the crRNA and the tracrRNA hybridize through the first and second complementary strands of the binding region for the Cas9 polypeptide,
   wherein the single-stranded protospacer sequence of the modified guide RNA hybridizes to a sequence in the target gene to be modified.
wherein the first modified guide RNA and the first biotinylated donor polynucleotide correct a first diseased allele,
wherein the second modified guide RNA and the second biotinylated donor polynucleotide correct a second diseased allele.

In an aspect, a method of treating a patient with an autosomal recessive disorder with compound heterozygous mutations comprises transplanting the cell made by the foregoing method.

In another aspect, a method of modifying a target gene in a patient or in a patient-derived cell, wherein the patient has Pompe disease, comprises
   delivering to the patient or cell a first modified guide RNA, a second modified guide RNA, a Cas9 polypeptide, a biotin-binding molecule, a first biotinylated donor polynucleotide, and a second biotinylated donor polynucleotide, wherein each modified guide RNA comprises,
      a crRNA comprising, a single-stranded protospacer sequence and a first complementary strand of a binding region for the Cas9 polypeptide, and
      a tracrRNA comprising a second complementary strand of the binding region for the Cas9 polypeptide,
      wherein the crRNA or the tracrRNA comprises an aptamer that binds a biotin-binding molecule,
      wherein the crRNA and the tracrRNA hybridize through the first and second complementary strands of the binding region for the Cas9 polypeptide,
      wherein the single-stranded protospacer sequence of the modified guide RNA hybridizes to a sequence in the target gene to be modified.
   wherein the first modified guide RNA and the first biotinylated donor polynucleotide correct a first diseased allele,
   wherein the second modified guide RNA and the second biotinylated donor polynucleotide correct a second diseased allele,
   wherein the single stranded protospacer region of the first modified guide RNA comprises CTCGTTGTCCAGGTAGGCCC (SEQ ID NO: 1) and the single stranded protospacer region of the second guide RNA comprises TGGACCACCAGCTCCTGTA (SEQ ID NO: 2).

In another aspect, a method of making an RNP complex, comprises
   selecting a single stranded protospacer sequence by identifying a mutant allele to be corrected, wherein the mutant allele is within 0 to 100 bases of a protospacer adjacent motif,
   producing a modified guide RNA comprising the selected single stranded protospacer region, wherein the modified guide RNA comprises
      a crRNA comprising the single-stranded protospacer sequence and a first complementary strand of a binding region for the Cas9 polypeptide, and
      a tracrRNA comprising a second complementary strand of the binding region for the Cas9 polypeptide,
      wherein the crRNA or the tracrRNA comprises an aptamer that binds a biotin-binding molecule,
      wherein the crRNA and the tracrRNA hybridize through the first and second complementary strands of the binding region for the Cas9 polypeptide,
   selecting a donor polynucleotide to correct the mutant allele and complementary to an anti-sense strand of genomic DNA, wherein the donor polynucleotide comprises a silent mutation in a constant region of the protospacer adjacent motif, e.g., within the final two nucleotides of the protospacer adjacent motif for *Streptococcus pyogenes*,
   producing a biotinylated donor polynucleotide, wherein the donor polynucleotide is biotinylated at the 5' end or the 3' end, and
   assembling the modified guide RNA, a Cas9 polypeptide, a biotin-binding molecule, and the biotinylated donor polynucleotide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1a is a schematic of the cause of Pompe disease. Pompe disease is caused by two defective copies of acid-α-glucosidase (GAA). This enzyme is responsible for breakdown of glycogen within lysosomes. Without GAA, glycogen build-up can cause downstream health issues. After correction, GAA expresses a functional protein leading to a reduction in lysosomal size.

FIG. 1b is a schematic of editing locations within the GAA locus. Pompe mutants are compound heterozygous at GAA. Allele one contains a point mutation that causes a premature stop codon (GAA:c.[1441=;2237G>A]) while allele two carries a one basepair deletion (GAA:c.[1441delT;2237=]). sgRNAs (underline) were designed to be specific to only the diseased allele by containing mutants (red) within the seed region. ssODNs used for genomic repair contained the wildtype sequence at the mutation site as well as a silent mutation (blue) to remove the PAM site (green) to prevent re-cutting of the corrected allele.

FIG. 4a shows the percentage of total sequencing reads from S1mplex-edited, primary fibroblasts from Pompe diseased patients. Results indicate gene correction and imprecise editing for 3 different mutations.

Figure 1C:
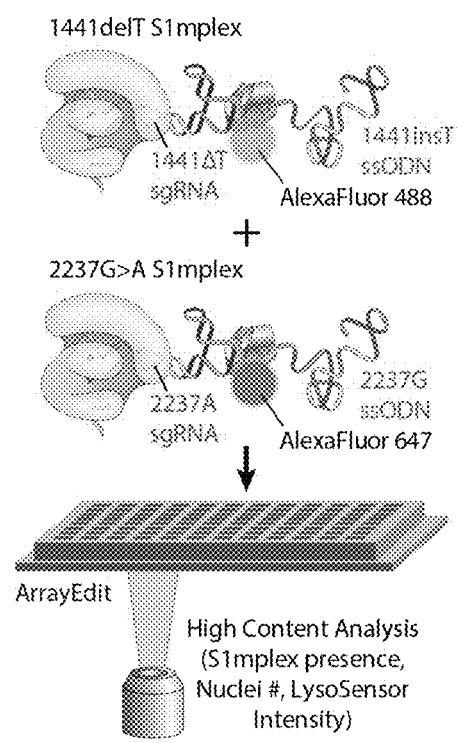
FIG. 1c is a schematic of S1mplex design for repair of compound heterozygous mutations. S1mplexes targeting the 1441delT mutant were labelled with an AlexaFluor®488 compound while S1mplexes targeting the 2237G>A mutation were labelled with an AlexaFluor®647. These RNP species were mixed prior to transfecting into cells and subsequently plated on ArrayEdit platform to conduct high-content analysis.

The above-described and other features will be appreciated and understood by those skilled in the art from the following detailed description, drawings, and appended claims.

DETAILED DESCRIPTION

For individuals with an autosomal recessive disease (e.g., cystic fibrosis, sickle cell anemia, and Tay-Sachs disease), the mutated gene is located on one of the nonsex chromosomes (autosomes), and both alleles of the gene carry mutations. The parents of an individual with symptoms of an autosomal recessive disease generally each carry one copy of the mutated gene, but they do not show obvious symptoms of the disease. Therefore, it has been assumed that correcting only one allele of the mutated gene would be sufficient to rescue the disease, and that additional genomic surgery to repair the second allele may subject a patient to undue risk. The inventors have tested this assumption with CRISPR-Cas9 gene editing to systematically correct both mutated alleles within the same cell from an autosomal recessive, infantile-onset case of Pompe disease. Unexpectedly, the inventors have shown that a CRISPR-Cas9 gene editing system can correct both mutated alleles.

The inventors previously developed a S1mplex strategy for modified guide RNAs such as sgRNAs and their RNP complexes with Cas9. The S1mplex tool exploits high affinity interactions between a short RNA aptamer and streptavidin to promote more faithful writing of the human genome. S1mplex modified guide RNAs or traditional guide RNAs can be used in the methods described herein.

In an aspect, these RNP-containing complexes can be assembled outside the cell to a desired stoichiometry and delivered as an all-in-one gene-editing nanoparticle together with a donor nucleic acid template. In addition, the complexes can be easily decorated with additional moieties such as fluorophores or Qdots to enrich for edited cells. Use of these particles with a biotinylated ssODN reduced heterogeneity in delivery among RNPs and nucleic acids within human cells and enriches the ratio of precisely-edited to imprecisely-alleles edited alleles up to 18-fold higher than standard RNP methods, approaching a ratio of four precise edits to every one imprecise edit. Further functionalization with a unique fluorophore enables multiplexed editing and enrichment of precisely edited populations through cell sorting. Taken together, advances with the S1mplex tool generates chemically-defined reagents to promote precise editing of the human genome.

The S1mplex strategy is inspired by CRISPR display that leverages structural studies of the RNP to identify locations in the sgRNA sequence where RNA aptamers could be tolerated.

CRISPR refers to the Clustered Regularly Interspaced Short Palindromic Repeats type II system used by bacteria and archaea for adaptive defense. This system enables bacteria and archaea to detect and silence foreign nucleic acids, e.g., from viruses or plasmids, in a sequence-specific manner. In type II systems, guide RNA interacts with Cas9 and directs the nuclease activity of Cas9 to target DNA sequences complementary to those present in the guide RNA. Guide RNA base pairs with complementary sequences in target DNA. Cas9 nuclease activity then generates a double-stranded break in the target DNA.

CRISPR/Cas9 is an RNP complex. CRISPR RNA (crRNA) includes a 20 base protospacer element that is complementary to a genomic DNA sequence as well as additional elements that are complementary to the transactivating RNA (tracrRNA). The tracrRNA hybridizes to the crRNA and binds to the Cas9 protein, to provide an active RNP complex. Thus, in nature, the CRISPR/Cas9 complex contains two RNA species.

sgRNA refers to a single RNA species which combines the tracrRNA and the crRNA and is capable of directing Cas9-mediated cleavage of target DNA. An sgRNA thus contains the sequences necessary for Cas9 binding and nuclease activity and a target sequence complementary to a target DNA of interest (protospacer sequence). In general, in an sgRNA, the tracrRNA and the crRNA are connected by a linker loop sequence. sgRNAs are well-known in the art. While sgRNA is generally used throughout this disclosure, two-part guide RNAs containing a crRNA and a tracrRNA can also be employed.

As used herein, a guide RNA protospacer sequence refers to the nucleotide sequence of a guide RNA that binds to a target DNA sequence and directs Cas9 nuclease activity to the target DNA locus. In some embodiments, the guide RNA protospacer sequence is complementary to the target DNA sequence. As described herein, the protospacer sequence of a single guide RNA may be customized, allowing the targeting of Cas9 activity to a target DNA of interest.

Any desired target DNA sequence of interest may be targeted by a guide RNA target sequence. Any length of target sequence that permits CRISPR-Cas9 specific nuclease activity may be used in a guide RNA. In some embodiments, a guide RNA contains a 20 nucleotide protospacer sequence.

In addition to the protospacer sequence, the targeted sequence includes a protospacer adjacent motif (PAM) adjacent to the protospacer region which is a sequence recognized by the CRISPR RNP as a cutting site. Without wishing to be bound to theory, it is thought that the only requirement for a target DNA sequence is the presence of a protospacer-adjacent motif (PAM) adjacent to the sequence complementary to the guide RNA target sequence. Different Cas9 complexes are known to have different PAM motifs. For example, Cas9 from *Streptococcus pyogenes* has a NGG trinucleotide PAM motif; the PAM motif of *N. meningitidis* Cas9 is NNNNGATT; the PAM motif of *S. thermophilus* Cas9 is NNAGAAW; and the PAM motif of *T. denticola* Cas9 is NAAAAC.

A modified guide RNA is a one-part or two-part RNA capable of directing Cas-9-mediated cleavage of target DNA. A modified sg RNA is a single RNA species capable of directing Cas9-mediated cleavage of target DNA. A modified sgRNA, for example, comprises sequences that provide Cas9 nuclease activity, a protospacer sequence complementary to a target DNA of interest, and an aptamer that binds a biotin-binding molecule. The linker loop that connects the tracrRNA and the crRNA in an sgRNA can be replaced with an aptamer that binds a biotin-binding molecule such as a streptavidin-binding aptamer. Unexpectedly, the modified sgRNAs can bind both Cas9 protein and streptavidin, and form active RNP complexes which induce error-prone DNA repair less frequently than standard CRISPR-Cas9 RNP complexes.

In an aspect, a modified guide RNA, comprises a crRNA comprising, a single-stranded protospacer sequence and a first complementary strand of a binding region for the Cas9 polypeptide, and a tracrRNA comprising a second complementary strand of the binding region for the Cas9 polypeptide, wherein the crRNA or the tracrRNA comprises an aptamer that binds a biotin-binding molecule, wherein the crRNA and the tracrRNA hybridize through the first and second complementary strands of the binding region for the Cas9 polypeptide, wherein the single stranded protospacer region comprises

CTCGTTGTCCAGGTAGGCCC, (SEQ ID NO: 1)

GGACCACCAGCTCCTGTAGG, (SEQ ID NO: 60)

GCCCAGGAAGCCGCAGACGT, (SEQ ID NO: 61)
or

-continued

CAGAGGAGCTGTGTGTGCAC (SEQ ID NO: 62)

TGGACCACCAGCTCCTGTAG. (SEQ ID NO: 2)

In another aspect, the crRNA and the tracrRNA form an sgRNA, the sgRNA comprising from 5' to 3',
the single-stranded protospacer sequence,
the first complementary strand of a binding region for the Cas9 polypeptide,
the aptamer that binds a biotin-binding molecule, and
the second complementary strand of the binding region for the Cas9 polypeptide.

More specifically, a modified sgRNA comprises, from 5' to 3', a single-stranded protospacer sequence, a first complementary strand of a binding region for the Cas9 polypeptide, an aptamer that binds a biotin-binding molecule, and a second complementary strand of the binding region of the Cas9 protein. In an embodiment, in the secondary structure of the modified sgRNA, the stem forms a stem-loop structure with the aptamer that binds the biotin-binding molecule.

In another aspect,
a crRNA comprises a single-stranded protospacer sequence and a first complementary strand of a binding region for the Cas9 polypeptide, and
a tracrRNA comprising a second complementary strand of the binding region for the Cas9 polypeptide,
wherein the crRNA and the tracrRNA hybridize through the first and second complementary strands of the binding region for the Cas9 polypeptide,
wherein the single stranded protospacer region comprises

CTCGTTGTCCAGGTAGGCCC, (SEQ ID NO: 1)

TGGACCACCAGCTCCTGTAG, (SEQ ID NO: 2)

GGACCACCAGCTCCTGTAGG, (SEQ ID NO: 60)

GCCCAGGAAGCCGCAGACGT, (SEQ ID NO: 61)
or

CAGAGGAGCTGTGTGTGCAC. (SEQ ID NO: 62)

The single-stranded protospacer region can comprise 17 to 20 nucleotides. Exemplary binding regions for Cas9 polypeptides comprise 10 to 35 base pairs.

In an aspect, the aptamer that binds a biotin-binding molecule forms a stem-loop structure. The stem portion of the stem-loop structure optionally forms a contiguous double strand with the double-stranded binding region for the Cas9 polypeptide. The stem portion of the aptamer can comprise 9 to 15 base pairs, while the loop comprises 30 nucleotides. The aptamer may contain more than one stem-loop structure. The length of the stem portion of the aptamer is not critical and can be adjusted depending on the application of the modified guide RNA.

A "Cas9" polypeptide is a polypeptide that functions as a nuclease when complexed to a guide RNA, e.g., an sgRNA or modified sgRNA. The Cas9 (CRISPR-associated 9, also known as Csn1) family of polypeptides, for example, when bound to a crRNA:tracrRNA guide or single guide RNA, are able to cleave target DNA at a sequence complementary to the sgRNA target sequence and adjacent to a PAM motif as described above. Cas9 polypeptides are characteristic of type II CRISPR-Cas systems. The broad term "Cas9" Cas9 polypeptides include natural sequences as well as engineered Cas9 functioning polypeptides. The term "Cas9 polypeptide" also includes the analogous Clustered Regularly Interspaced Short Palindromic Repeats from *Prevotella* and *Francisella* 1 or CRISPR/Cpf1 which is a DNA-editing technology analogous to the CRISPR/Cas9 system. Cpf1 is an RNA-guided endonuclease of a class II CRISPR/Cas system. This acquired immune mechanism is found in *Prevotella* and *Francisella* bacteria. Additional Class I Cas proteins include Cas3, Cas8a, Cas5, Cas8b, Cas8c, Cas 10d, Case1, Cse 2, Csy 1, Csy 2, Csy 3, GSU0054, Cas 10, Csm 2, Cmr 5, Cas10, Csx11, Csx10, and Csf 1. Additional Class 2 Cas9 polypeptides include Csn 2, Cas4, C2c1, C2c3 and Cas13a.

Exemplary Cas9 polypeptides include Cas9 polypeptide derived from *Streptococcus pyogenes*, e.g., a polypeptide having the sequence of the Swiss-Prot accession Q99ZW2 (SEQ ID NO: 3); Cas9 polypeptide derived from *Streptococcus thermophilus*, e.g., a polypeptide having the sequence of the Swiss-Prot accession G3ECR1 (SEQ ID NO: 4); a Cas9 polypeptide derived from a bacterial species within the genus *Streptococcus*; a Cas9 polypeptide derived from a bacterial species in the genus *Neisseria* (e.g., GenBank accession number YP_003082577; WP 015815286.1 (SEQ ID NO: 5)); a Cas9 polypeptide derived from a bacterial species within the genus *Treponema* (e.g., GenBank accession number EMB41078 (SEQ ID NO: 6)); and a polypeptide with Cas9 activity derived from a bacterial or archaeal species. Methods of identifying a Cas9 protein are known in the art. For example, a putative Cas9 protein may be complexed with crRNA and tracrRNA or sgRNA and incubated with DNA bearing a target DNA sequence and a PAM motif.

The term "Cas9" or "Cas9 nuclease" refers to an RNA-guided nuclease comprising a Cas9 protein, or a fragment thereof (e.g., a protein comprising an active, inactive, or partially active DNA cleavage domain of Cas9, and/or the gRNA binding domain of Cas9). In some embodiments, a Cas9 nuclease has an inactive (e.g., an inactivated) DNA cleavage domain, that is, the Cas9 is a nickase. Other embodiments of Cas9, both DNA cleavage domains are inactivated. This is referred to as catalytically-inactive Cas9, dead Cas9, or dCas9.

Functional Cas9 mutants are described, for example, in US20170081650 and US20170152508, incorporated herein by reference for its disclosure of Cas9 mutants.

In addition, to the modified sgRNA and the Cas9 polypeptide or active fragment thereof, an RNP complex may further comprise a biotin-binding molecule such as an avidin such as avidin, streptavidin, or neutravidin which bind with high affinity to the aptamer that binds the biotin-binding molecule in the modified sgRNA. Avidin, streptavidin and neutravidin are a tetramers and each subunit can bind biotin with equal affinity. Avidin, streptavidin and neutravidin variants that contain one, two or three biotin binding sites are also available and may be employed in the complex.

When the RNP complex comprises a biotin-binding molecule, the complex can further comprise a biotinylated molecule which associates with the complex via the biotin-binding molecule. The biotinylated molecule can target the RNP complex to a specific cell type, organ or tissue. For example, PEG-coated gold nanoparticles exhibit size-dependent in vivo toxicity; the renal clearance of quantum dots can be controlled; and the accumulation of PEGylated silane-coated magnetic iron oxide nanoparticles has been shown to be size dependent.

In one embodiment, the biotinylated molecule is a biotinylated oligodeoxynucleotide, such as a biotinylated donor DNA template. Homologous recombination can insert an exogenous polynucleotide sequence into the target nucleic acid cleavage site. An exogenous polynucleotide sequence can be called a donor polynucleotide or a donor sequence. In some embodiments, a donor polynucleotide, a portion of a donor polynucleotide, a copy of a donor polynucleotide, or a portion of a copy of a donor polynucleotide can be inserted into a target nucleic acid cleavage site. A donor polynucleotide can be single-stranded DNA, double-stranded DNA, RNA, or a duplex of RNA and DNA. A donor polynucleotide can be a sequence that does not naturally occur at a target nucleic acid cleavage site. In some embodiments, modifications of a target nucleic acid due to NHEJ and/or HDR can lead to, for example, mutations, deletions, alterations, integrations, gene correction, gene replacement, transgene insertion, nucleotide deletion, gene disruption, and/or gene mutation. The process of integrating non-native nucleic acid(s) into genomic DNA can be referred to as "genome engineering".

In an embodiment, the biotinylated molecule is a nanoparticle, such as a quantum dot, a gold particle, a magnetic particle, a polymeric nanoparticle. In another embodiment, the biotinylated molecule is a biotinylated fluorescent dye such as Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, Alexafluor® 488 biocytin, Alexafluor® 546, Alexa Fluor® 549, lucifer yellow cadaverine biotin-X, *Lucifer* yellow biocytin, Oregon green 488 biocytin, biotin-rhodamine and tetramethylrhodamine biocytin. Biotinylated molecule may also be a peptide, proteins or protein domains, specifically antibodies and Fab domains.

In another embodiment, the biotinylated donor polynucleotide comprises a contrast agent, a cell targeting ligand, a tissue targeting ligand, or a peptide.

In another aspect, the biotin-binding molecule can be covalently linked to a donor polynucleotide, a nanoparticle, or a dye molecule either directly or via a linker molecule, using, for example a disulfide linker. The bound biotin-binding molecule can then bind the aptamer of the modified sgRNA. Additional biotinylated donor polynucleotides, nanoparticle, contrast agent, or dye molecules can then be associated with the bound biotin-binding molecule. Alternatively, the biotin-binding molecule can be associated with the biotinylated molecule prior to adding to modified sgRNA.

A method of modifying a target gene in a patient or in a patient-derived cell, wherein the patient has an autosomal recessive disorder with compound heterozygous mutations comprises
 delivering to the patient or cell a first modified guide RNA, a second modified guide RNA, a Cas9 polypeptide, a biotin-binding molecule, a first biotinylated donor polynucleotide, and a second biotinylated donor polynucleotide, wherein each modified guide RNA comprises,
  a crRNA comprising, a single-stranded protospacer sequence and a first complementary strand of a binding region for the Cas9 polypeptide, and
  a tracrRNA comprising a second complementary strand of the binding region for the Cas9 polypeptide,
  wherein the crRNA or the tracrRNA comprises an aptamer that binds a biotin-binding molecule,
  wherein the crRNA and the tracrRNA hybridize through the first and second complementary strands of the binding region for the Cas9 polypeptide,
 wherein the single-stranded protospacer sequence of the modified guide RNA hybridizes to a sequence in the target gene to be modified.
 wherein the first modified guide RNA and the first biotinylated donor polynucleotide correct a first diseased allele,
 wherein the second modified guide RNA and the second biotinylated donor polynucleotide correct a second diseased allele.

Exemplary patient-derived cells comprises an induced pluripotent stem cell, a progenitor cell, a mesenchymal stem cell, or a tissue-specific stem cell. Exemplary tissue-specific stem cells comprises a skeletal stem cell, a hematopoietic stem cell, an epithelial stem cell, or a neural stem cell.

In an embodiment, a first RNP complex comprises the first modified guide RNA, the Cas9 polypeptide, the biotin-binding molecule and the first biotinylated donor polynucleotide; and a second RNP complex comprises the second modified guide RNA, the Cas9 polypeptide, the biotin-binding molecule and the second biotinylated donor polynucleotide.

In another embodiment, the first modified guide RNA, the second modified guide RNA and the Cas9 polypeptide are expressed from one or more viral vectors. For example, a first viral vector expresses the first modified guide RNA, and a second viral vector expresses the second modified guide RNA, and a third viral vector expresses the Cas9 polypeptide.

Exemplary patients are human patients. Exemplary human autosomal recessive disorders are aspartylglucosaminuria, Batten disease, cystinosis, Fabry disease, Gaucher Disease Type I, II or III, Pompe Disease, Tay Sachs Disease, Sandhoff Disease, Metachromatic leukodystrophy, Mucolipidosis Type, I, II/III or IV, Hurler Disease, Hunter disease, Sanfilippo disease Types A,B,C,D, Morquio disease Types A and B, Maroteaux-Lamy disease, Sly disease, Niemann-Pick Disease Types A/B, C1 or C2, or Schindler Disease Types I or II.

In an embodiment, the autosomal recessive disorder is a human lysosomal storage disorder, such as Pompe disease.

A method of treating a patient with an autosomal recessive disorder with compound heterozygous mutations comprises transplanting the cell made by the methods described herein into the subject. Lysosomal storage diseases are caused by an inborn error of metabolism that results in the absence or deficiency of an enzyme, leading to the inappropriate storage of material in various cells of the body. Most lysosomal storage disorders are inherited in an autosomal recessive manner.

In an embodiment, modifying the target gene increases or decreases the expression of a gene product of the target gene.

In another embodiment, modifying the target gene comprises high-fidelity homology-directed repair (HDR).

In another embodiment, modifying the target gene comprises the addition of a genetic functionality, or the correction of a mutation.

In yet another embodiment, modifying the target gene creates a double strand break (DSB) which is repaired by a non-homologous end joining (NHEJ) cell repair mechanism generating indels thereby modifying the polynucleotide sequence of the target gene.

In a further embodiment, modifying the target gene creates a DSB which is repaired by a homologous recombination (HDR) cell repair mechanism incorporating a donor DNA sequence thereby modifying the polynucleotide sequence of the target gene.

In another aspect, the S1m-sgRNAs described herein can be used for the excision of genomic DNA. In an aspect, two S1m-sgRNAs can be employed simultaneously, wherein each S1m-sgRNA targets an end of the region to be excised. As shown in Example 12, human cells contain the properly excised region of genomic DNA Delivery of polynucleotides and RNPs of the present disclosure to cells, in vitro, or in vivo, may be achieved by a number of methods known to one of skill in the art. These methods include lipofection, electroporation, nucleofection, microinjection, biolistics, liposomes, immunoliposomes, polycation or lipid:nucleic acid conjugates. Lipofection is well known and lipofection reagents are sold commercially. Cationic and neutral lipids that are suitable for efficient receptor-recognition lipofection of polynucleotides are described in the art.

Lipid:nucleic acid complexes, including targeted liposomes such as immunolipid complexes, and the preparation of such complexes is well known to one of skill in the art.

Electroporation can be used to deliver the polynucleotides and RNPs of the present disclosure. In these methods, the polynucleotides or RNPs are mixed in an electroporation buffer with the target cells to form a suspension. This suspension is then subjected to an electrical pulse at an optimized voltage, which creates temporary pores in the phospholipid bilayer of the cell membrane, permitting charged molecules like DNA and proteins to be driven through the pores and into the cell. Reagents and equipment to perform electroporation are sold commercially.

Biolistic, or microprojectile delivery, can be used to deliver the polynucleotides and RNPs of the present disclosure. In these methods, microprojectiles, such as gold or tungsten, are coated with the polynucleotide by precipitation with calcium chloride, spermidine or polyethylene glycol. The microprojectile particles are accelerated at high speed into a cell using a device such as the BIOLISTIC® PDS-1000/He Particle Delivery System (Bio-Rad; Hercules, Calif.).

In another embodiment, a viral vector expressing the modified guide RNA of the present disclosure, a viral vector expressing a Cas9 polypeptide and biotinylated donor DNA template (e.g., a biotinylated donor DNA template), can be transfected into a cell, such as a human cell. Human cells include human pluripotent stem cell lines and primary blood cell such as hematopoietic stem and progenitor cells and T-cells. Once editing has occurred in the cell line, the cells can be differentiated and transplanted into a subject, or used for drug development.

In some embodiments, the polynucleotides of the present disclosure may also comprise modifications that, for example, increase stability of the polynucleotide. Such modifications may include phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and amino alkylphosphoramidates, phosphorodiamidates, thionophosphoramidates, thionoalkylphosphonates, thionoalkylphosphotriesters, selenophosphates, and boranophosphates having normal 3'-5' linkages, 2-5' linked analogs, and those having inverted polarity wherein one or more internucleotide linkages is a 3' to 3', a 5' to 5' or a 2' to 2' linkage. Exemplary nucleic acid-targeting polynucleotides having inverted polarity can comprise a single 3' to 3' linkage at the 3'-most internucleotide linkage (i.e. a single inverted nucleoside residue in which the nucleobase is missing or has a hydroxyl group in place thereof). Various salts (e.g., potassium chloride or sodium chloride), mixed salts, and free acid forms can also be included.

In some embodiments, the polynucleotides of the present disclosure may also contain other nucleic acids, or nucleic acid analogues. An example of a nucleic acid analogue is peptide nucleic acid (PNA).

In an embodiment, a method of modifying a target gene in a patient or in a patient-derived cell, wherein the patient has Pompe disease, comprises
  delivering to the patient or cell a first modified guide RNA, a second modified guide RNA, a Cas9 polypeptide, a biotin-binding molecule, a first biotinylated donor polynucleotide, and a second biotinylated donor polynucleotide, wherein each modified guide RNA comprises,
    a crRNA comprising, a single-stranded protospacer sequence and a first complementary strand of a binding region for the Cas9 polypeptide, and
    a tracrRNA comprising a second complementary strand of the binding region for the Cas9 polypeptide,
    wherein the crRNA or the tracrRNA comprises an aptamer that binds a biotin-binding molecule,
    wherein the crRNA and the tracrRNA hybridize through the first and second complementary strands of the binding region for the Cas9 polypeptide,
    wherein the single-stranded protospacer sequence of the modified guide RNA hybridizes to a sequence in the target gene to be modified.
  wherein the first modified guide RNA and the first biotinylated donor polynucleotide correct a first diseased allele,
  wherein the second modified guide RNA and the second biotinylated donor polynucleotide correct a second diseased allele,
  wherein the single stranded protospacer region of the first modified guide RNA
  comprises CTCGTTGTCCAGGTAGGCCC (SEQ ID NO: 1) and the single stranded
  protospacer region of the second guide RNA comprises TGGACCACCAGCTCCTGTA (SEQ ID NO: 2).

In another embodiment, a method of modifying a target gene in a patient or in a patient-derived cell, wherein the patient has Pompe disease, comprises
  delivering to the patient or cell a first guide RNA, a second guide RNA, a Cas9 polypeptide, a first donor polynucleotide, and a second donor polynucleotide, wherein each guide RNA comprises,
    a crRNA comprising, a single-stranded protospacer sequence and a first complementary strand of a binding region for the Cas9 polypeptide, and
    a tracrRNA comprising a second complementary strand of the binding region for the Cas9 polypeptide,
    wherein the crRNA and the tracrRNA hybridize through the first and second complementary strands of the binding region for the Cas9 polypeptide,
    wherein the single-stranded protospacer sequence of the modified guide RNA hybridizes to a sequence in the target gene to be modified.

wherein the first guide RNA and the first donor polynucleotide correct a first diseased allele,
wherein the second guide RNA and the second donor polynucleotide correct a second diseased allele,
wherein the single stranded protospacer region of the first modified guide RNA comprises CTCGTTGTCCAGGTAGGCCC (SEQ ID NO: 1) and the single stranded protospacer region of the second guide RNA comprises TGGACCACCAGCTCCTGTA (SEQ ID NO: 2).

Also included herein are methods of making RNP complexes, specifically first and second RNP complexes that provide biallelic correction. In an embodiment, a method of making an RNP complex, comprises selecting a single stranded protospacer sequence by identifying a mutant allele to be corrected, wherein the mutant allele is within 0 to 100 bases of a protospacer adjacent motif, producing a modified guide RNA comprising the selected single stranded protospacer region, wherein the modified guide RNA comprises a crRNA comprising the single-stranded protospacer sequence and a first complementary strand of a binding region for the Cas9 polypeptide, and a tracrRNA comprising a second complementary strand of the binding region for the Cas9 polypeptide, wherein the crRNA or the tracrRNA comprises an aptamer that binds a biotin-binding molecule, wherein the crRNA and the tracrRNA hybridize through the first and second complementary strands of the binding region for the Cas9 polypeptide, selecting a donor polynucleotide to correct the mutant allele and complementary to an anti-sense strand of genomic DNA, wherein the donor polynucleotide comprises a silent mutation in a constant region of the protospacer adjacent motif, e.g., within the final two nucleotides of the protospacer adjacent motif for *Streptococcus pyogenes*, producing a biotinylated donor polynucleotide, wherein the donor polynucleotide is biotinylated at the 5' end or the 3' end, and assembling the modified guide RNA, a Cas9 polypeptide, a biotin-binding molecule, and the biotinylated donor polynucleotide.

In an embodiment, the donor polynucleotide is asymmetric around a cut site. In another embodiment, the method further comprises repeating the method and producing a second RNP complex, wherein the second RNP complex corrects a second mutant allele to result in a biallelic correction.

The invention is further illustrated by the following non-limiting examples.

EXAMPLES

Methods
Cell Culture:

All hPSCs were maintained in mTeSR1™ medium on Matrigel® (WiCell) coated tissue culture polystyrene plates (BD Falcon). Cells were passaged every 4-5 days at a ratio of 1:8 using Versene™ solution (Life Technologies). Patient derived human induced pluripotent stem cell line Pompe GM04192 was a gift from the T. Kamp and M. Suzuki (UW-Madison) labs. Cardiomyocytes derived from hPSC and iPSC cultures were maintained in RPMI/B27 on Matrigel® (WiCell) coated polystyrene plates (BD Falcon). Patient derived fibroblast lines were obtained from Coriell Institute with different GAA mutations and cultured in DMEM supplemented with 10% FBS and 1% Penicillin/Streptomycin. All cells were maintained at 37° C. in 5% $CO_2$, and tested monthly for possible *mycoplasma* contamination.

Cardiomyocyte Differentiation:

hPSCs and iPSCs were differentiated into cardiomyocytes using a small molecule-directed differentiation protocol in a 12-well plate format as previously described. Briefly, all adherent hPSCs and iPSCs were dissociated in TrypLE™ solution (Life Technologies), counted with a hemocytometer, and centrifuged at 200×g for 5 minutes. Cells were plated at a density between $0.5-1×10^6$ cells/well depending on cell line. Once tissue culture plate wells reached 100% confluency (day 0), medium in each well was replaced with a solution containing ml RPMI/B27-Insulin (Life Technologies), 12 μM CHIR99021 (BioGems 25917), and 1 μg/ml Insulin solution (Sigma-Aldrich 19278). Exactly 24 hours later (day 1) medium in each well was removed and replaced with RPMI/B27-insulin. Exactly 48 hours after (day 3) half of the spent medium was collected. To this, an equal volume of fresh RPMI/B27-Insulin was mixed. This combined media was then supplemented with 7.5 μM IWP2 (BioGems 75844). Two days later (day 5) medium in each well was replaced with RPMI/B27-Insulin. Two days (day 7) later and every three days following, spent medium was replaced with RPMI/B27. Spontaneous contraction was generally observed between days 12-16 of differentiation.

Creation of S1m-sgRNAs:

S1m-sgRNAs were synthesized as previously described. S1m gBlocks were annealed with Phusion™ polymerase (New England Biolabs) under the following thermocycler conditions: 98° C. for 30 sec followed by 30 cycles at 98° C. for 10 s, and 72° C. for 15 s with a final extension at 72° C. for 10 minutes. S1m cDNA was annealed with Phusion™ polymerase (New England Biolabs) under the following thermocycler conditions: 98° C. for 30 sec followed by 30 cycles at 98° C. for 10 s, 60° C. for 10 s, and 72° C. for 15 s with a final extension at 72° C. for 10 minutes. In vitro transcription was performed with the MEGAShortscript™ T7 Kit (Thermo Fisher Scientific) according to manufacturer's instructions.

For guides for fibroblast transfection, in vitro transcription was performed using HiScribe™ T7 RNA synthesis Kit (New England Biolabs).

Genome Editor Deliver:

All hPSC transfections were performed using the 4D-Nucleofector System™ (Lonza) in P3 solution using protocol CA-137. 50 pmol Cas9, 60 pmol sgRNA, 50 pmol streptavidin, and 60 pmol ssODN were used to form particles per ssODN-S1mplex as described above. Cells were then harvested using TrypLE™ (Life Technologies) and counted. $2×10^5$ cells per transfection were then centrifuged at 100×g for 3 minutes Excess media was aspirated and cells were resuspended using 20 μL of RNP solution per condition. After nucleofection, samples were incubated in nucleocuvettes at room temperature for 15 minutes prior to plating into $2*10^4$ cells per well on ArrayEdit in mTeSR™ media+10 μM ROCK inhibitor. Media was changed 24 hours post transfection and replaced with mTeSR™ medium. Fibroblast transfections were performed in 24 well plates using 50,000 cells/well using 2 μl Lipofectamine® 2000/well (0.5 μg Cas9/well and sgRNA, streptavidin and ssODN at a 1:1:1:1 molar ratio).

Synthesis of ArrayEdit Platform:

μCP was performed using previously described methods. The surface modification involved printing of an alkanethiol initiator to nucleate the polymerization of hydrophilic poly (ethylene glycol) (PEG) chains. Briefly, double sided-adhesive was attached to the bottom of a standard tissue culture plate, after which a laser cutter was used to cut out the well bottoms. Using previously described chemistry, patterns were transferred to gold-coated glass via a polydimethylsiloxane stamp after which the glass was submerged in a poly(ethylene glycol) (PEG) solution overnight to build hydrophilic PEG chains surrounding µFeatures. Standard tissue culture plates with well bottoms cut out were then fastened to processed sheets using a custom-made alignment device.

High-Content Analysis:

Automated microscopy was performed using a Nikon Eclipse TI epifluorescent scope. A 20×20 grid with one µFeature per image was established and maintained so that each feature imaged was consistent each day. Nikon Perfect Focus was used to ensure that all colonies were in the same Z-plane and LysoSensor™ intensity was measured accurately. Images were processed using CellProfiler™ to count the number of nuclei and quantify LysoSensor™ intensity.

Genomic Sequencing:

DNA was isolated from cells using DNA QuickExtract™ (Epicentre) following TrypLE™ treatment and centrifugation. Extracted DNA was incubated at 65° C. for 15 min, 68° C. for 15 min, and 98° C. for 10 min. Genomic PCR was performed using AccuPrime™ HiFi Taq (Life Technologies) and 500 ng of genomic DNA according to manufacturer's instructions. Long (8 kb) PCR reactions were thermocycled using an extension step of 10 minutes. All genomic PCR products were then submitted to the University of Wisconsin-Madison Biotechnology Center for DNA sequencing.

RT- and qPCR:

RNA was isolated from cells using RNA QuickExtract™ (Epicentre) following the manufacturer's protocol. 100 ng of extracted RNA was reverse transcribed using Superscript® IV Reverse Transcriptase (Invitrogen). Endpoint PCR amplification of the cDNA product was performed following the manufacturer's instructions using AccuPrime™ HiFi Taq (Life Technologies) and 1 µl of cDNA Product. Efficacy of the endpoint PCR was performed via gel electrophoresis of the PCR product in a 1% agarose gel.

The qPCR reaction was set up in triplicate for each cell line and sequence (GAPDH, dT, 746, and GAA), by mixing 10 µl iTaq™ Universal SYBR® Green Supermix (Bio-Rad), 0.5 µl sequence specific forward primer, 0.5 µl sequence specific reverse primer, 1 µl cDNA product, and 8 µl water. qPCR analysis was performed in a CFX96 Real Time PCR System under the following thermocycling conditions: 95° C. for 30 s followed by 35 cycles of 95° C. for 5 s, and 60° C. for 30 s, with a melt curve analysis increasing stepwise from 65° C. to 95° C. in increments of 0.5° C.

Next Generation Sequencing Analysis:

A custom python script was developed to perform sequence analysis. For each sample, sequences with frequency of less than 1000 were filtered from the data. Sequences in which the reads matched with primer and reverse complement subsequences classified as "target sequences". Target sequences were aligned with corresponding wildtype sequence using global pairwise sequence alignment. The frequency, length, and position of matches, insertions, deletions, and mismatches were all tracked in the resulting aligned sequences.

Western Blotting:

Protein expression of GAA and β-Actin was determined in each cell line. Following cell lysis in ice-cold RIPA buffer supplemented with protease and phosphatase inhibitors and EDTA (5 mM), protein concentration was determined (DC Protein Assay, BioRad). Forty µg of protein from each cell line was loaded into a 4-12% Bis-Tris precast gel (Criterion XT, BioRad) and gel electrophoresis performed. Proteins were then transferred to a nitrocellulose membrane and blocked in filtered 5% nonfat dry milk in TBS-T (Tris buffered saline, 0.15% Tween20) for 1 hour at room temperature. The membrane was then incubated overnight at 4° C. with GAA (Abcam ab137068, 1:1000) and β-Actin (Millipore, MAB1501, 1:40,000) primary antibodies. Following the incubation period, the membrane was washed in TBS-T and incubated with appropriate horseradish peroxidase secondary antibodies (Goat Anti-Rabbit IgG, Abcam ab205718, 1:2000; Anti-Mouse IgG, Cell Signaling Technologies 7076 1:20,000) for 1 hour. The membrane was washed again in TBS-T, and then developed (SuperSignal™ West Pico Plus Chemiluminescent Substrate, Thermo Scientific) for 5 minutes using a ChemiDoc-It™2 Imaging System (UVP) and imaged.

GAA Activity Assay:

Acid glucosidase activity was measured by hydrolysis of 4-methylumbelliferyl—D-glucoside (4-MUG, Sigma M-9766) at pH 4 to release the fluorophore 4-methylumbelliferone (4-MU) as previously described. Briefly, 4-MUG was incubated with 10 µL protein lystate in 0.2M sodium acetate for one hour at 37° C. Fluoresence was then measured using a Glomax® plate reader (Progmega) and activity was calculated using a standard curve.

Immunocytochemistry:

Live cell imaging of lysosome intensity was done using LysoSensor™ Green (Life Technologies L7535). Dye was mixed in culture media at a 1:1000 dilution prior to adding media to wells. Cells were then incubated for 5 minutes in LysoSensor™ solution. Media was then aspirated and cells were washed 2× with PBS. All imaging was done within one hour of staining.

To assay for pluripotency markers, hPSC cultures were fixed using 4% PFA and incubated at room temperature for 10 minutes. Cells were then permeabilized using 0.05% Triton™ X-100 and incubated for 10 minutes. Following two washes with 5% goat serum, NANOG antibody (R&D Systems AF1997, 1:200) and TRA-1-60 antibody (Millipore MAB5360, 1:150), was added to cells and incubated overnight at 4° C. The next day, cells were rinsed twice with 5% goat serum and then incubated with a donkey anti-goat secondary antibody (Life Technologies A11055 1:500) for one hour at room temperature. Cells were then washed twice with PBS and mounted for imaging.

Cardiomyocyte cultures were processed in the same manner as above. After permeabilization, cells were incubated with anti-sarcomeric alpha-actinin (Abcam ab68167 1:250) overnight at 4° C. The next day, cells were rinsed twice with 5% goat serum and then incubated with a goat anti-rabbit secondary antibody (Santa Cruz Biotech sc-362262, 1:500.

Media Exchange:

Cardiomyocytes were cultured in RPMI/B27+insulin and media was exchanged every two days. As a normal media exchange, diseased and corrected cells were introduced to RPMI/B27+insulin/−glucose. 24 hours post change, cells were stained with LysoSensor™ as described above to determine a baseline fluorescent intensity. After staining, media was replaced with media from either corrected or healthy lines and cultured for an additional 24 hours. After incubation, cells were again stained with LysoSensor™ and imaged using confocal microscopy.

Isolation of Corrected iPSCs:

On day one post plating, we measured the presence of S1mplex within the nucleus as well as identified μFeatures that contained only one cell to ensure clonal populations. On days two through six, we measured the number of cells to obtain a growth rate via day over day change. Finally, on day 7, we measured the number of cells as well as stained cells with LysoSensor™ to identify populations that may have been edited using phenotypic recovery as a marker. We also mock transfected WA09 and Pompe iPSCs and plated them on ArrayEdit and subjected them to the same high content analysis as a control. After 7 days we plotted each individual μFeature by its LysoSensor™ intensity and growth rate and color coded each feature by the presence of S1mplexes on day 1. We observed a large population of clones that grew slower than the slowest mock transfected Pompe colonies suggesting that that population may undergo editing events. By comparing LysoSensor™ intensity we also observed that many of the μFeatures within the wells had higher, and therefore more acidic organelles than mock transfected Pompe iPSCs. In fact, many of the μFeatures had similar intensities to control WA09 colonies. By combining these data with the presence of S1mplexes we were able to select colonies that were potentially preferably edited at either loci individually or both simultaneously. Using this knowledge, we selected colonies of interest for expansion and analysis.

Following expansion of selected clones, we analyzed each one at both loci for the correction of mutations. We also designed the introduction of a PAM codon wobble to ensure that supplied donor DNA was the source for repair. When we looked at colonies that only had the presence of one S1mplex on day 1 we obtained clones that were edited at the specified allele. Interestingly we did not isolate any clones that had indel mutations caused by NHEJ. Further, colonies that were positive for one S1mplex were not observed to be edited at the other locus. We next analyzed clones positive for both S1mplexes and managed to obtain a clone that was edited at both alleles and also contained the PAM wobble. There was also one colony that contained one PAM mutation while the other allele was repaired but did not introduce the novel mutation. Importantly, across all screened clones we did not obtain any that contained indel products. We then selected one clone from each population (edited at either allele individually, or both) to assay for phenotypic recovery.

Example 1: Correction of Two Diseased Alleles within Pompe iPSCs

To explore whether two corrected endogenous alleles within the same cell is possible, several clonal isogenic iPSC lines were generated by CRISPR-Cas9 gene editing of an iPSC line derived from a patient with infantile-onset Pompe disease. In this line, compound heterozygous GAA mutations responsible for the disease phenotype are a deletion of a thymidine nucleotide at position 1441 (GAA:c.[1441delT], "1441delT") causing a frameshift, and premature stop codon on one allele, and a G>A conversion at nucleotide 2237 (GAA:c.[2237G>A], "2237G>A") forming an immediate stop codon on the other (FIG. 1b). The mutations within GAA in this patient are ~6.1 kb apart, and hence using a single double strand break (DSB) with homology directed repair from a long plasmid or viral donor would likely be inefficient. We therefore used a strategy utilizing two distinct Cas9 ribonucleoproteins (RNPs) with accompanying single stranded oligonucleotide (ssODN) templates encoding the gene correction. (FIG. 1b, Tables 1-2)

TABLE 1

Protospacer and respective PAMs used for genomic targeting.

| Name | Protospacer | SEQ ID NO: | PAM |
|---|---|---|---|
| 1441delT sgRNA | CTCGTTGTCCAGGTAGGCCC | 7 | GGG |
| 2237G>A sgRNA | TGGACCACCAGCTCCTGTAG | 8 | GGG |
| W746X sgRNA | GGACCACCAGCTCCTGTAGG | 60 | GGG |
| D645N sgRNA | GCCCAGGAAGCCGCAGACGT | 61 | TGG |
| R660H sgRNA | CAGAGGAGCTGTGTGTGCAC | 62 | TGG |

TABLE 2 ssODNs used to direct HDR after DSB Formation.

| Name | Sequence (5'-3') | SEQ ID NO: |
|---|---|---|
| 1441insT ssODN | CTTCCATGCAGGCCCTGGGTGGGGCCGGGTCTCCCCA CTGCAGCCTCTCGTTGTCCAGGTATGGCCCGGATCCAC TGCCTTCCCCGACTTCACCAACCCC | 9 |
| 2237A>G ssODN | TGCCCATCCCCCTTGCAGGTTCCCCAAGGACTCTAGCA CCTGGACTGTGGACCACCAGCTCCTGTGGGGAGAGGC CCTGCTCATCACCCCAGTGCTCCAG | 10 |
| W746X ssODN | TGCCCATCCCCCTTGCAGGTTCCCCAAGGACTCTAGCA CCTGGACTGTGGACCACCAGCTCCTGTGGGGAGAGGC CCTGCTCATCACCCCAGTGCTCCAG | 63 |
| D645N ssODN | AGAAATCCTGCAGTTTAACCTGCTGGGGGTGCCTCTG GTCGGGGCAGACGTCTGTGGCTTCCTGGGCAACACCT CAGAGGAGCTGTGTGTGCACTGGACC | 64 |
| R660H ssODN | GGGCCAACGTCTGCGGCTTCCTGGGCAACACCTCAGA GGAGCTATGTGTGCGCTGGACCCAGCTGGGGGCCTTC TACCCCTTCATGCGGAACCACAACAG | 65 |

Figure 1D:
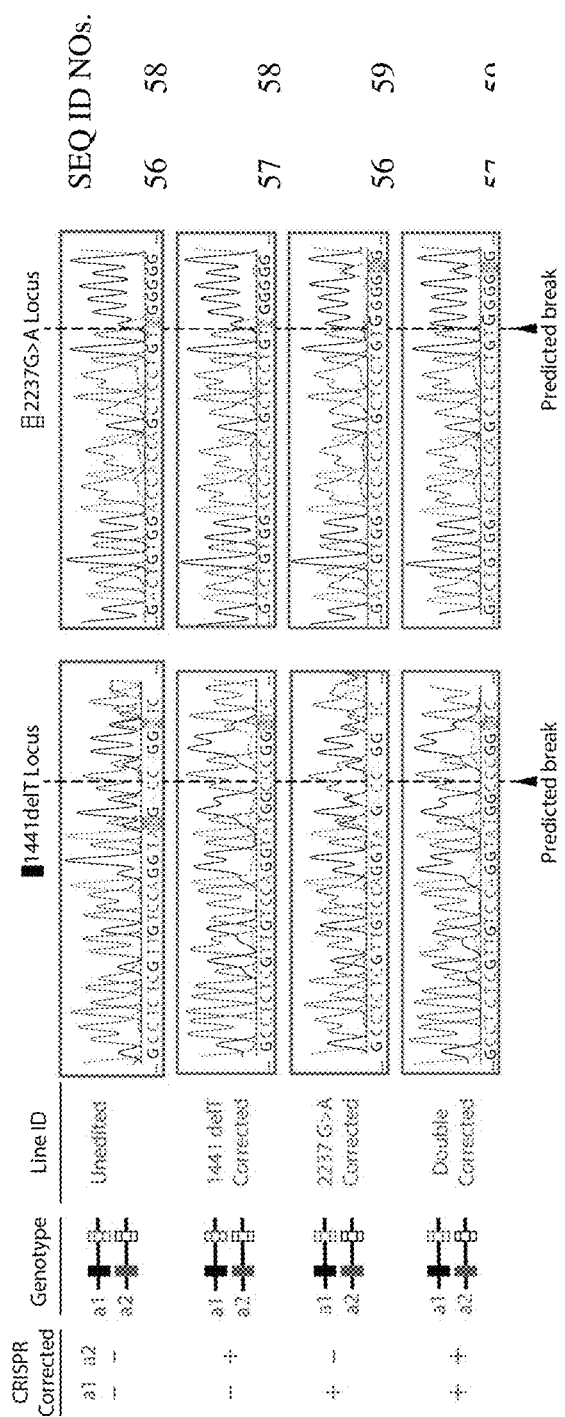
FIG. 1d shows Sanger sequencing traces of all corrected lines. The unedited line contains mutations at both alleles: 1441delT mutation causes a breakdown of sequence trace, whereas a single point mutation demonstrates a heterozygosity 2237G>A locus. Single corrected clones remain identical to unedited line at unedited locus and contained PAM wobble on the corrected allele. Double corrected line contained PAM wobble at both loci. Wobble A bases in the corrected lines are highlighted to indicate repair from the ssODN. SpCas9 cut site denoted by dotted line, and sequencing chromatograms do not show evidence of undesired NHEJ products.
Figure 5:
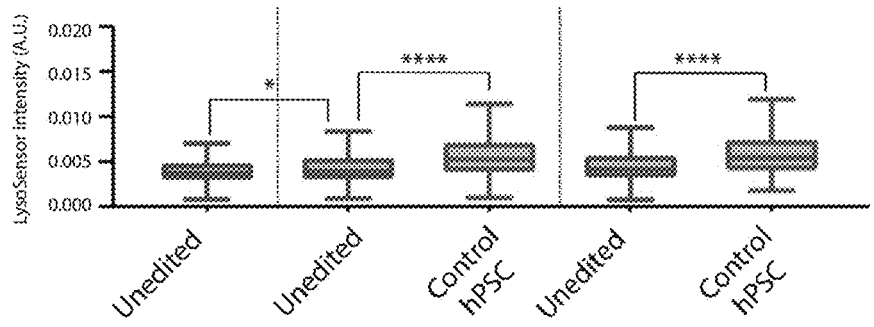
FIG. 5 shows quantification of LysoSensor™ intensity in each co-culture condition. LysoSensor™ intensity was measured on a per-cell basis using confocal microscopy. Control hPSCs had significantly higher intensity than unedited cells in all conditions. Unedited cells co-cultured with hPSCs also had an increased LysoSensor™ intensity when compared to those cultured alone (*p<0.05, ****p<0.001).
Figure 6:
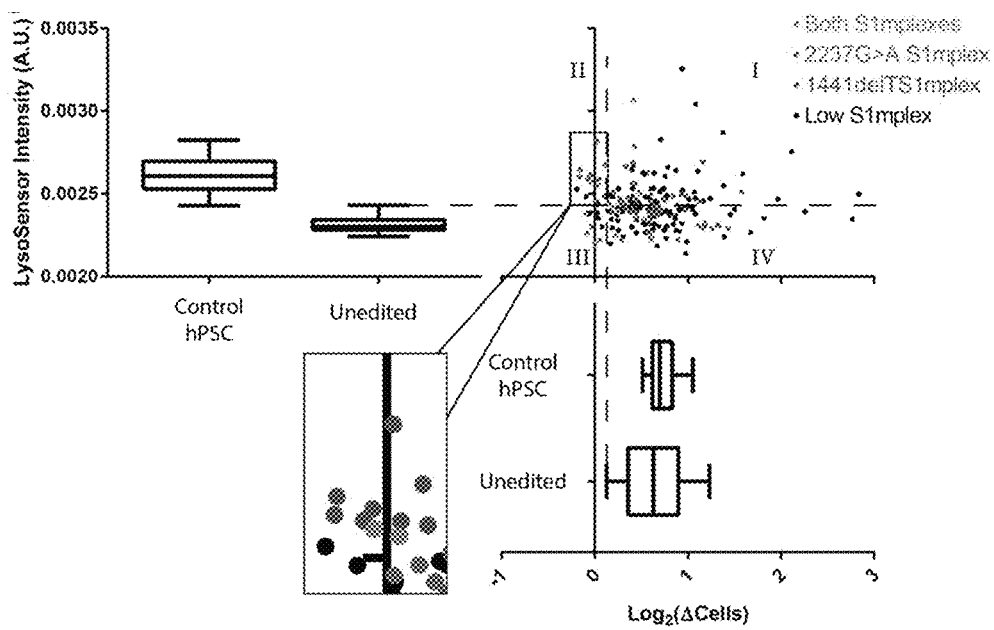
FIG. 6 shows Left: LysoSensor™ quantification per µFeature of two mock transfections after 7 days of growth. hPSCs were significantly more intense than unedited iPSCs on ArrayEdit. Bottom Right: Growth rate of unedited and control hPSCs following a mock transfection to establish a baseline for growth. Growth rates were calculated by measuring the per-day change in the number of cells of the µFeature. Features were graphed as an average of these per day changes. Top Right: LysoSensor™ intensity was plotted against growth rate per µFeature to identify edited colonies. Individual plotted colonies were also assayed for presence of either genome editor (represented in either purple or green), both genome editors (red) and low amounts of genome editors (black). Colonies of interest are identified as those with high genome editor expression and lower growth rates, presumably arising from the stress of genome editing. Dashed lines indicate regions of interest. Also included is a magnification of quadrant II from panel. µFeatures in this region were selected for genomic analysis to isolate edited clones.

Specifically, using a combination of S1mplex and ArrayEdit technologies developed by our lab, we enriched for properly-edited iPSCs after delivery of the two genome editors by tracking the presence of genome editors within the nucleus (FIG. 1c). Using high-content analysis imaging of the iPSC clones during culture post delivery of the editors, we tracked the growth rate of clones, as well as screening the pH of the lysosome using a Lysosensor™ dye. Lysosensor™ is sensitive to the buildup of glycogen in the diseased lysosome of mutant GAA cells, as high glycogen neutralizes this otherwise acidic organelle (FIG. 1c; FIGS. 5-6). We isolated cell lines that were corrected at the 1441delT allele and the 2237G>A allele individually (FIG. 1d, termed 'single corrected'). We also isolated a clone corrected at both GAA:c.[1441delT];[2237G>A] alleles (FIG. 1d, termed 'double corrected').

Figure 4A:
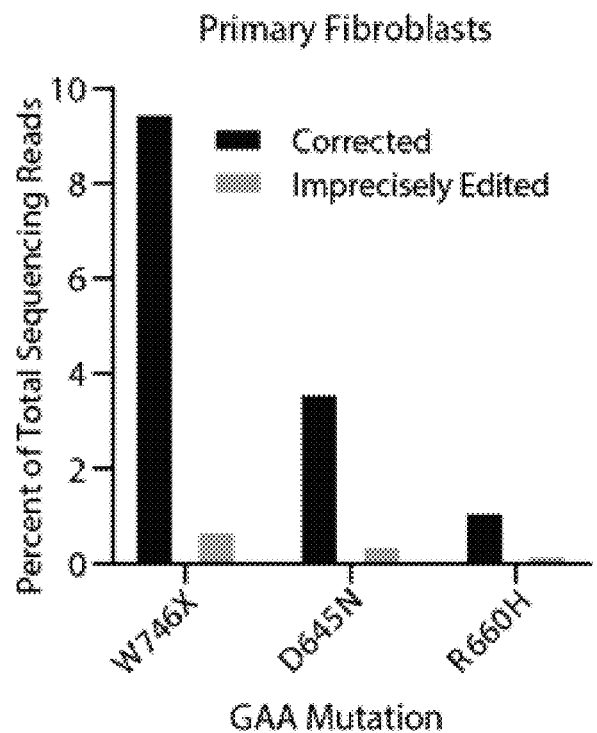
FIGS. 4a and b show highly precise gene correction using S1mplex strategy in primary fibroblasts from three Pompe disease patients.
Figure 4B:
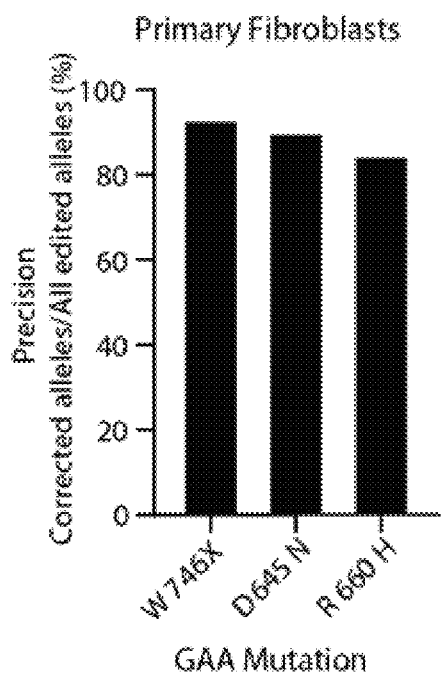
FIG. 4b shows that percentage of edited alleles that are precisely edited, indicating that S1mplex genome editors can perform as precise-90 editors. Primary fibroblasts were obtained from Coriell Institute. W746X mutation was from Coriell ID: GM04912. D645N mutation was from Coriell ID: GM20090. R660H was from Coriell ID: GM13522.
Figure 7:
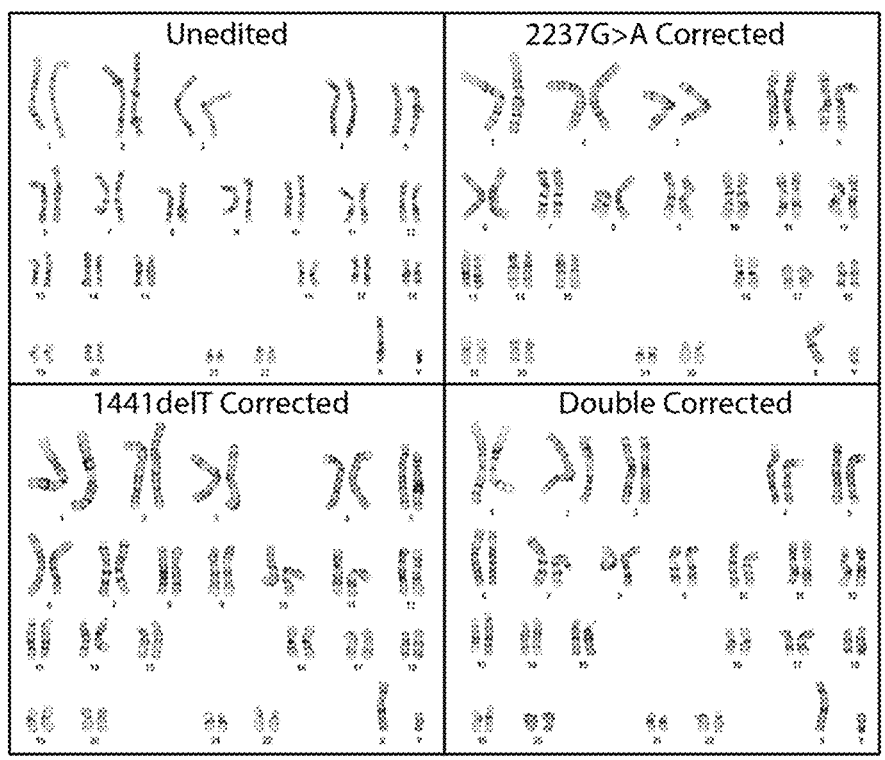
FIG. 7 shows karyotypes of all isolated gene-corrected lines as well as unedited cells. No abnormalities were detected at a band resolution of 500.
Figure 8:
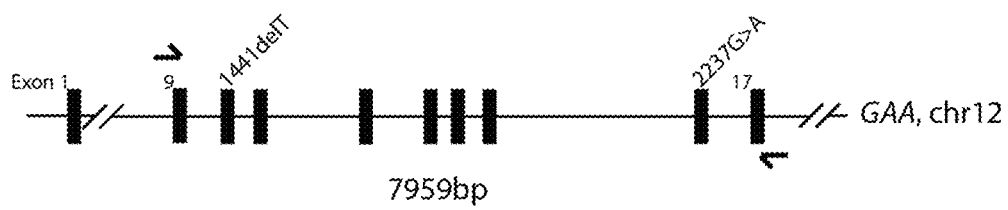
FIG. 8 shows a schematic for long PCR covering both Cas9 cut sites. Primers are denoted by arrows. The expected PCR amplicon is 7959 bp in length.
Figure 9:
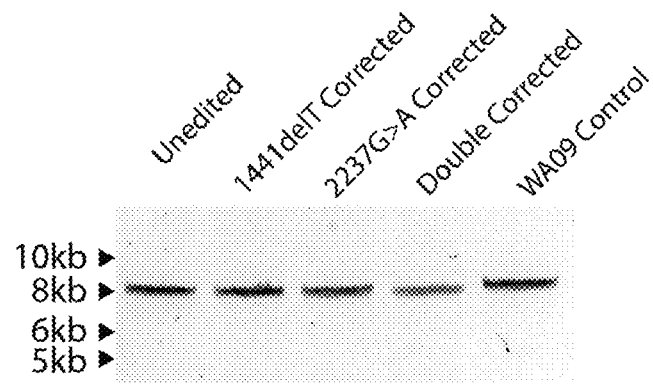
FIG. 9 shows a gel analysis of long range PCR described in panel c and FIG. 2a in each isolated cell line. No significant deviances from the expected length were detected, and no other significant bands were observed. WA09 control cells are hPSCs.
Figure 10:
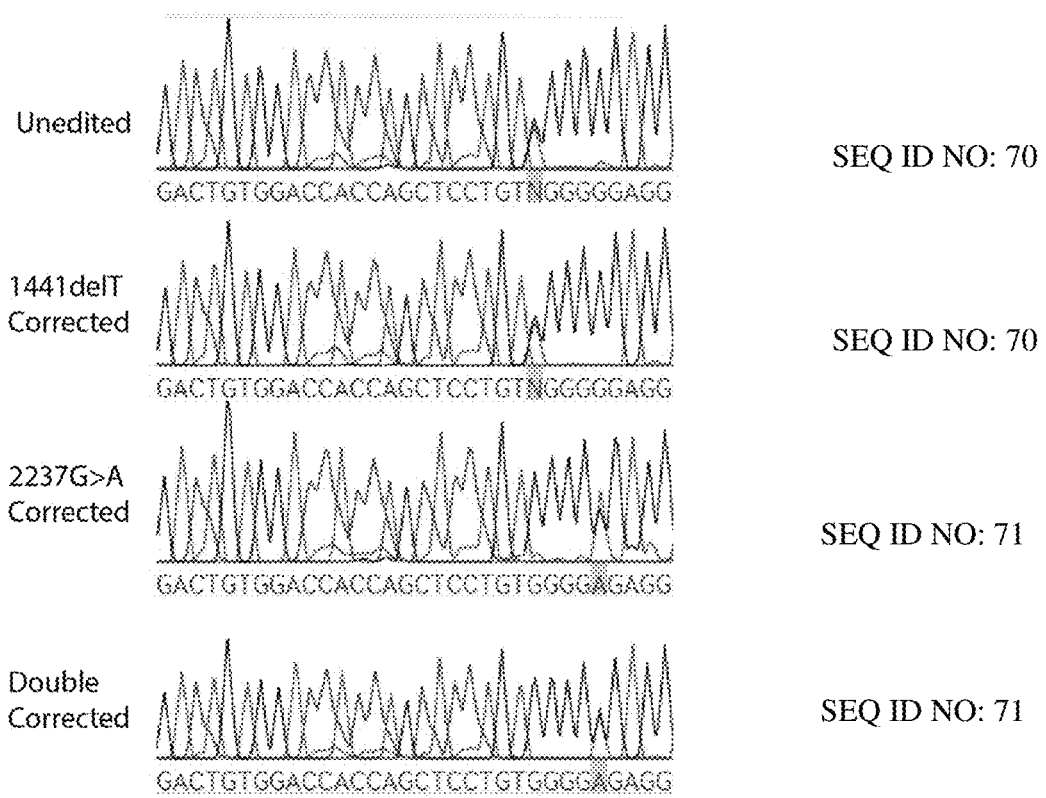
FIG. 10 shows Sanger sequencing traces of long range PCR shown in panel FIG. 9. SNPs were observed showing that PCR products were a result of amplification from both alleles within the cells.

All gene-corrected lines remained pluripotent, and after karyotyping each of the isolated lines, we observed no large transversions or inversions (FIG. 7). Because genome editing can create large indel mutations, we also conducted an 8 kb PCR on GAA that included both sgRNA target sites and observed no genomic deletions between the sgRNA target sites. (FIG. 8, 9) Sequencing of these large PCR amplicons confirmed that both alleles were present and no other sequence abnormalities were detected at the edited loci. (FIG. 10) Finally, chromatograms from Sanger sequencing at the top three off-target sites for each sgRNA matched the untransfected, patient-derived cell line, indicating that none of the top off-target regions were modified by our editing strategy (Table 3). Similar S1mplex strategies generated edits at 84-93% precision at the sgRNA target in primary fibroblasts derived from other Pompe diseased patients (FIG. 4).

TABLE 3

Off-target sequencing results

| Off-target site | Correction | Sequence | SEQ ID NO: |
|---|---|---|---|
| 2237 OT-1 | Unedited | CCTCCCTTCCTAGACCACCAGCTCCTGCAGGAGGGCTTGG | 72 |
| | 1441delT Corrected | CCTCCCTTCCTAGACCACCAGCTCCTGCAGGAGGGCTTGG | 72 |
| | 2237G>A Corrected | CCTCCCTTCCTAGACCACCAGCTCCTGCAGGAGGGCTTGG | 72 |
| | Double Corrected | CCTCCCTTCCTAGACCACCAGCTCCTGCAGGAGGGCTTGG | 72 |
| 2237 OT-2 | Unedited | GCCCCTGCCTCTACAGGAGCAGGTGGTGAGGATGGCTCCG | 73 |
| | 1441delT Corrected | GCCCCTGCCTCTACAGGAGCAGGTGGTGAGGATGGCTCCG | 73 |
| | 2237G>A Corrected | GCCCCTGCCTCTACAGGAGCAGGTGGTGAGGATGGCTCCG | 73 |
| | Double Corrected | GCCCCTGCCTCTACAGGAGCAGGTGGTGAGGATGGCTCCG | 73 |
| 2237 OT-3 | Unedited | CACGCTGCCACGACAGGAGCTGCTGGTCAACTCCTCCTCT | 74 |
| | 1441delT Corrected | CACGCTGCCACGACAGGAGCTGCTGGTCAACTCCTCCTCT | 74 |
| | 2237G>A Corrected | CACGCTGCCACGACAGGAGCTGCTGGTCAACTCCTCCTCT | 74 |
| | Double Corrected | CACGCTGCCACGACAGGAGCTGCTGGTCAACTCCTCCTCT | 74 |
| 1441 OT-1 | Unedited | CCCCGTATCCCTGGTTGTCCAGGTGGGCCCTGGGAGAACA | 75 |
| | 1441delT Corrected | CCCCGTATCCCTGGTTGTCCAGGTGGGCCCTGGGAGAACA | 75 |
| | 2237G>A Corrected | CCCCGTATCCCTGGTTGTCCAGGTGGGCCCTGGGAGAACA | 75 |
| | Double Corrected | CCCCGTATCCCTGGTTGTCCAGGTGGGCCCTGGGAGAACA | 75 |
| 1441 OT-2 | Unedited | CAGCTGCCGTCTCGATGGCCAGGTAGGCCTGGGCAAGGAC | 76 |
| | 1441del1 Corrected | CAGCTGCCGTCTCGATGGCCAGGTAGGCCTGGGCAAGGAC | 76 |
| | 2237G>A Corrected | CAGCTGCCGTCTCGATGGCCAGGTAGGCCTGGGCAAGGAC | 76 |
| | Double Corrected | CAGCTGCCGTCTCGATGGCCAGGTAGGCCTGGGCAAGGAC | 76 |
| 1441 OT-3 | Unedited | AATTAGGCTAGGGCCTACCTGGTCAATAATGAAATAATTG | 77 |
| | 1441delT Corrected | AATTAGGCTAGGGCCTACCTGGTCAATAATGAAATAATTG | 77 |
| | 2237G>A Corrected | AATTAGGCTAGGGCCTACCTGGTCAATAATGAAATAATTG | 77 |
| | Double Corrected | AATTAGGCTAGGGCCTACCTGGTCAATAATGAAATAATTG | 77 |

Figure 2A:
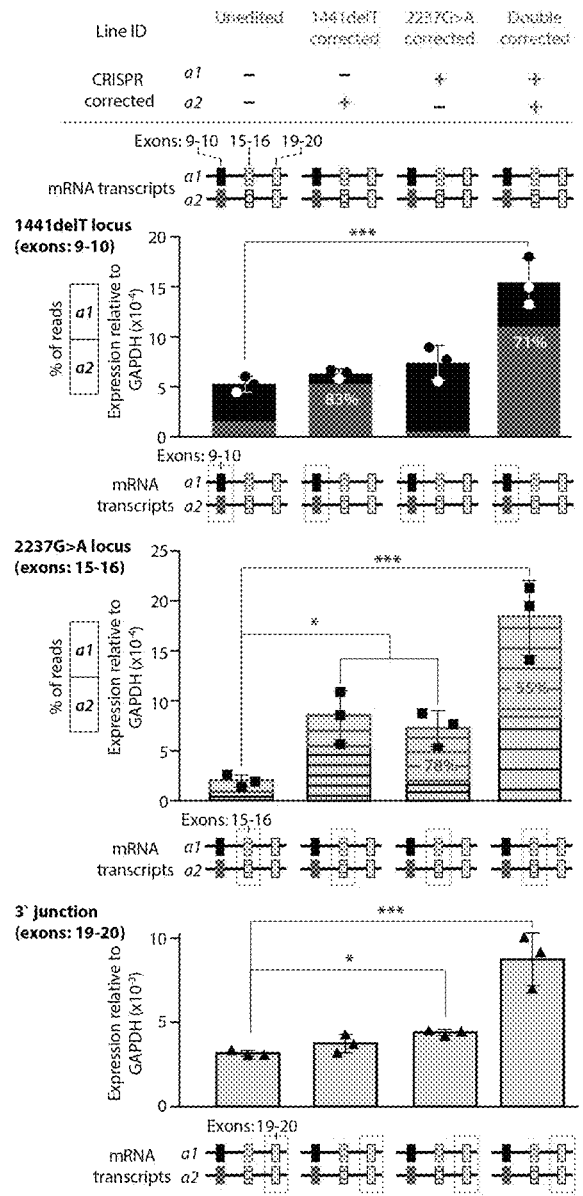
FIG. 2a, top panel, is a schematic of GAA mRNA used for qRT-PCR. mRNA was analyzed at 3 locations, around the 1441delT locus (solid), the 2237G>A locus (hashed), and at the final 3' junction (outlined). The middle two panels show an overlay of qRT-PCR and deep sequencing data around each edited locus: analysis around 1441delT loci (solid bars) and analysis around 2237G>A locus (hashed bars). Bars are color coded by sequence identity, either wildtype, mutant, or corrected, from deep sequencing analysis. Bar heights are equivalent to qRT-PCR quantification relative to GAPDH. In all corrected lines, the corrected allele was expressed at a higher frequency than the unedited allele. Double corrected line expressed the highest level of overall mRNA and expressed each allele at approximately equal amounts. The bottom panel shows quantification of total GAA mRNA in unedited, single corrected, and double corrected lines via qRT-PCR. The double corrected line had a significantly higher amount of mRNA than any of the other isolated line (n=3 technical replicates). This is consistent with expression from two active alleles (*p<0.05 ***p<0.005, two-tailed t-test, $\alpha$=0.05, heteroscedastic). Bar graphs are plotted with standard deviation.

Quantitative RT-PCR (qRT-PCR) at the 3' end of the GAA mRNA transcript as well as around each edited locus (FIG. 2a) indicated that the corrected loci were correctly expressed. We observed that the unedited line expressed the lowest levels of GAA when compared to internal GAPDH levels (FIG. 2a), despite the presence of full-length, mature mRNA that could be used to express protein (FIG. 2a). The single corrected lines also expressed mature mRNA, while the double corrected line contained approximately a 2-fold increase in GAA transcripts. We confirmed that double-corrected cell lines consistently produced greater amounts of mature mRNA than any other condition (FIG. 2a) by conducting qPCR at both edited loci.

Figure 2B:
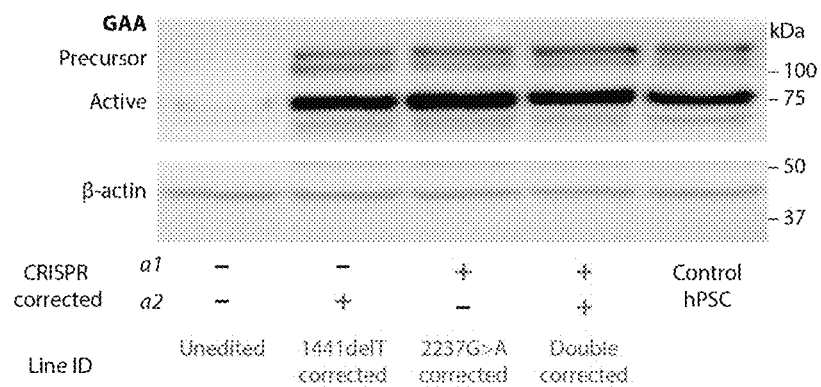
FIG. 2b shows a Western blot for GAA protein. Each of the corrected lines expressed high levels of active protein as well as detectable levels of precursor protein. Unedited cells expressed significantly lower levels of GAA protein but was still above the limit of detection.
Figure 2C:
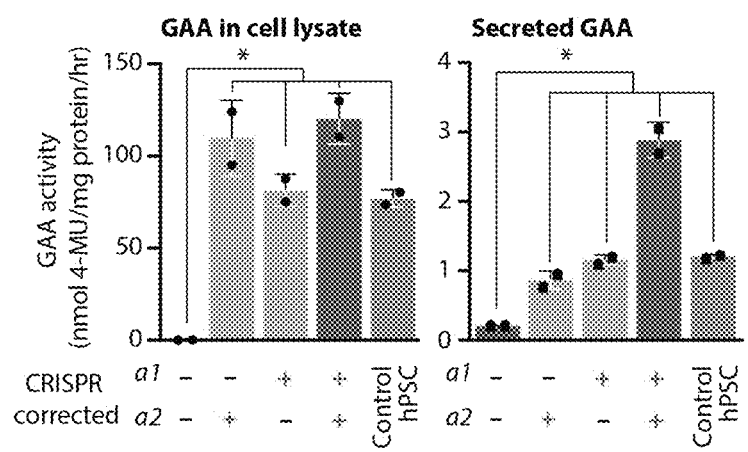
FIG. 2c shows GAA activity in cell lysate and cell culture media supernatant as measured by 4-MUG cleavage in acidic conditions. Unedited cells were unable to cleave this substrate, showing there was little to no active protein. All corrected lines had significantly higher activity than unedited cells but were indistinguishable from each other (n=2 technical replicates, *p<0.05, two-tailed t-test, $\alpha$=0.05, heteroscedastic; Bar graphs plotted with standard deviation).

By looking for the presence of disease variants and protoadjacent motif (PAM) wobbles introduced by the ssODN (FIG. 1b) via deep sequencing on endpoint PCR samples of mRNA, we observe that both alleles are expressed individually at higher levels (3-5 fold increase) than unedited cells (FIG. 2a). Each allele is expressed similarly to the corresponding single corrected line (FIG. 2a). These findings suggest nonsense mediated decay of the mutant transcript or cellular compensation to overcome the mutant allele within the single corrected lines. We detected active GAA protein using a Western blot (FIG. 2b) at levels comparable to a control hPSC line. We were also able to identify precursor polypeptides, which are important to protein secretion, showing the GAA transcripts from the edited alleles are being correctly translated and processed within cells. Notably, we are able to detect only small amounts of GAA protein and precursor polypeptides in the unedited iPSCs. All edited cell lines were able to secrete active GAA (FIG. 2c).

Example 2: Enzymatic Cross-Correction by Gene-Corrected Cells

Figure 3A:
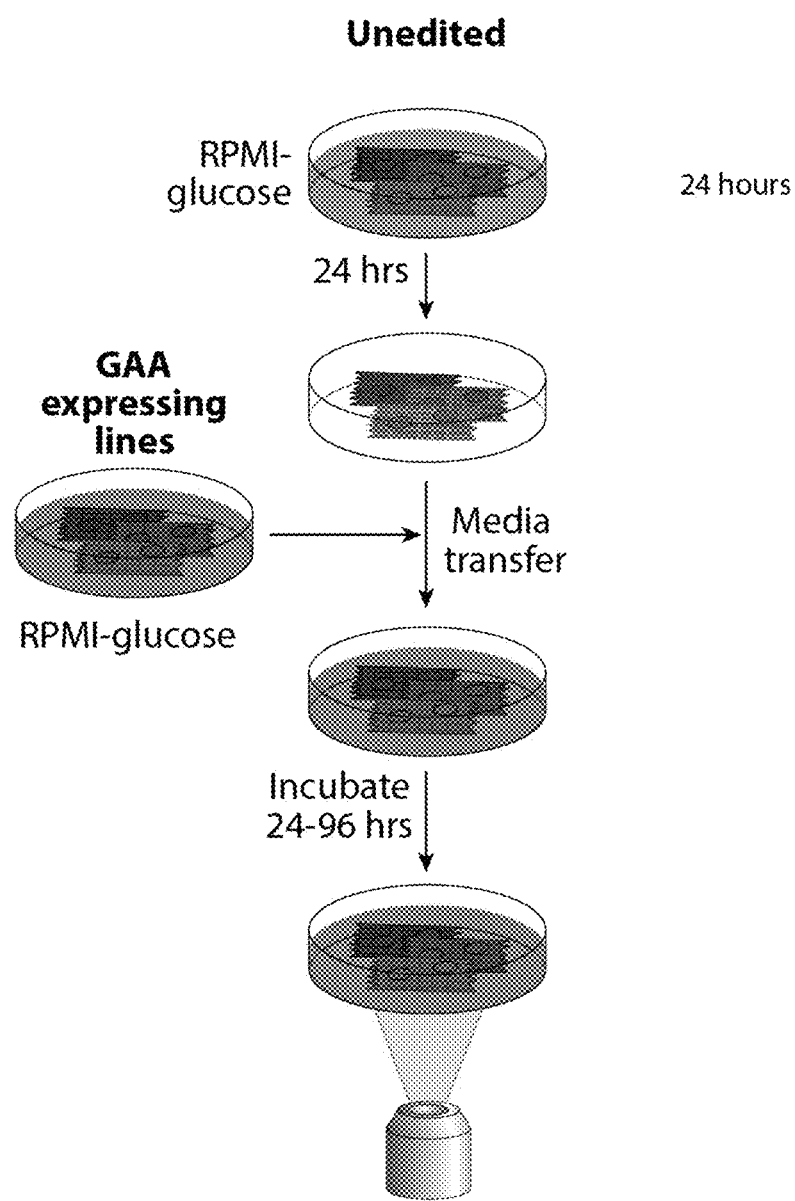
FIG. 3a is a schematic of enzymatic cross-correction experiments using gene-corrected cardiomyocytes. Unedited iPSC-CMs (red) were supplied media without glucose for 24 hours (orange). After 24 hours media was replaced with media (pink) that had previously been exposed to corrected cell lines (blue) or supplemented with rhGAA. 96 hours after replacement, unedited cells were stained with LysoSensor™ and imaged using confocal microscopy for dye intensity.
Figure 3B:
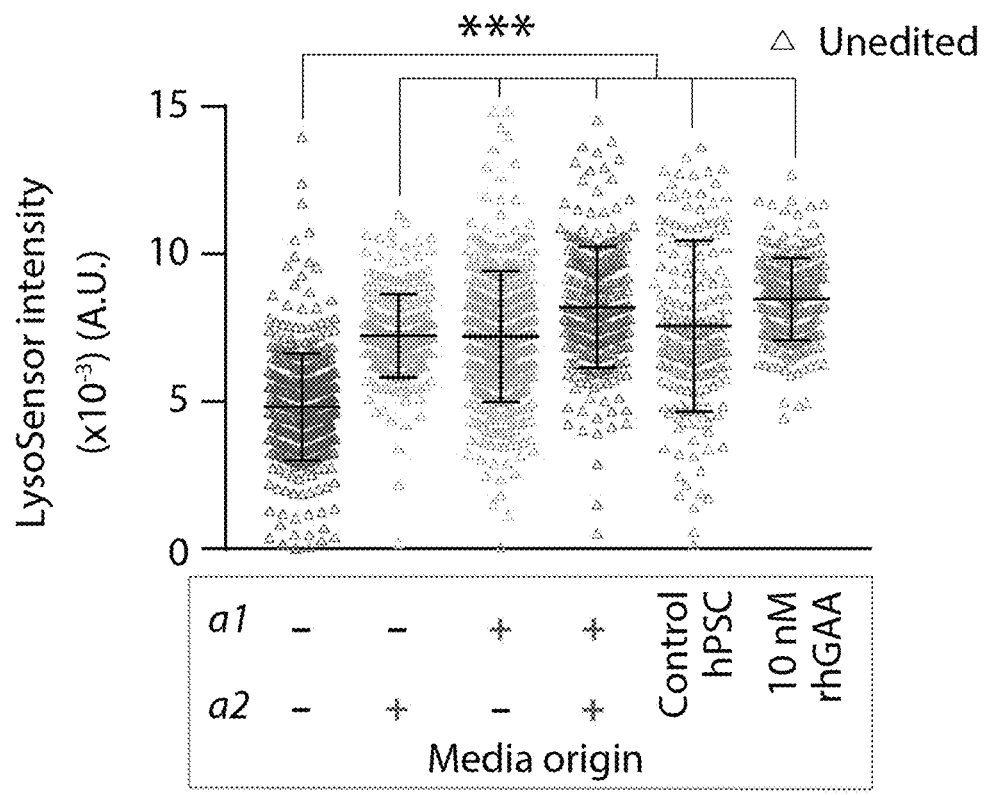
FIG. 3b shows quantification of LysoSensor™ intensity in cross-corrected lines 96 hours post media exchange. Each triangle represents a corrected cell identified using CellProfiler™. After 96 hours of daily media changes or supplementing with rhGAA all conditions had significant increase in dye intensity over control conditions. Unedited cells were modified to express histone 2B (H2B)-mCherry to facilitate imaging of the nuclei in these assays. (***p<0.005, n>134, two-tailed t-test, $\alpha$=0.05, heteroscedastic; bar graphs plotted with standard deviation).
Figure 3C:
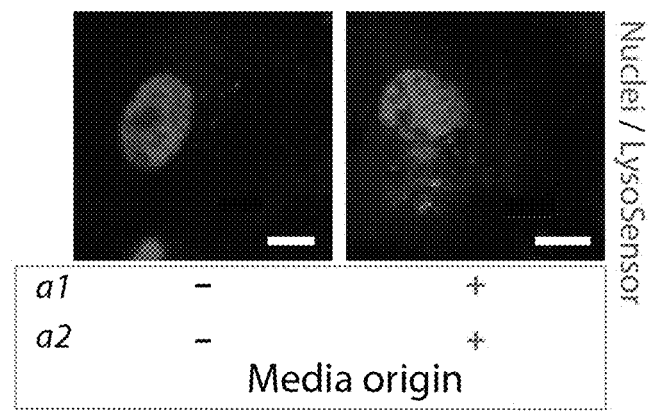
FIG. 3c shows representative images of unedited iPSC-CMs stained with LysoSensor™ in media from unedited and double corrected iPSC-CMs.
Figure 3D:
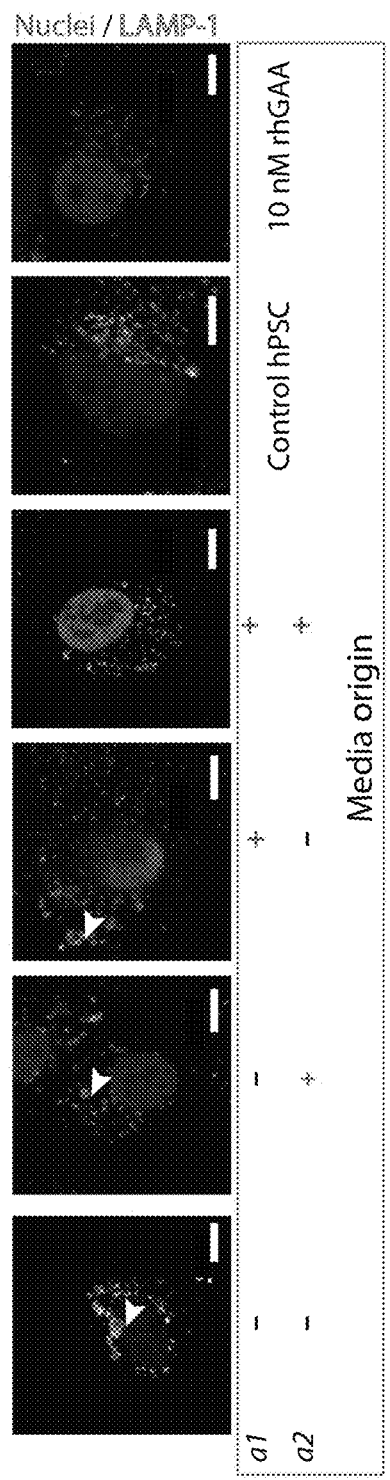
FIG. 3d shows representative images of LAMP1 staining in unedited, single corrected, double corrected cells and control PSC-CM and unedited iPSC-CM treated with rhGAA. (scale bars: 10 µm).

Detection of active GAA secretion led us to test the potential of edited cells to enzymatically cross-correct diseased cells (FIG. 3a). Because Pompe disease has a significant effect on cardiac tissue in infants, we differentiated all iPSC lines to cardiomyocytes (Pompe iPSC-CMs) using a previously described small-molecule inhibitor protocol (FIG. 3a). For all differentiations, we observed spontaneous contraction and confirmed the expression of α-actinin, a marker of cardiac lineage commitment. Similar to results seen in the iPSC state, differentiated corrected lines still expressed and secreted active GAA, as indicated in a 4-MUG cleavage assay on cardiomyocyte protein lysates and spent culture media. It has previously been demonstrated that by culturing in medium devoid of glucose, Pompe iPSC-CMs display an accumulation of glycogen within the lysosome. We performed a medium exchange experiment wherein we took partially spent, glucose-free medium from each corrected line (putatively containing secreted active GAA) and used it to replace glucose-free medium on unedited Pompe iPSC-CMs (FIG. 3a). One day after this media exchange, cells were stained with LysoSensor and subsequent confocal microscopy was used to measure lysosome acidity as a proxy for glycogen clearance. As a control we added rhGAA to unedited Pompe iPSC-CMs to simulate ERT. When unedited cardiomyocytes were supplemented with 10 nM rhGAA (ERT), LysoSensor™ intensity increased, indicating a clearance of glycogen from the lysosome. Media from all edited cells were able to recover the lysosomal pH at 96 hr (FIG. 3b), and this clearance is expected to continue until normal levels of glycogen were reached. Within these cultures, lysosomal size of unedited Pompe iPSC-CMs in GAA-positive media was profiled through visualization of Lysosomal Associated Membrane Protein 1, (LAMP-1). In media from unedited cells, lysosomes were enlarged, consistent with buildup of glycogen (FIG. 3c). In comparison, when media was taken from double-corrected cells or supplemented with rhGAA, lysosomes appeared as punctae. Samples from single corrected cells fell between these two extremes. Taken together, the single- and double-corrected cells enzymatically cross-correct diseased cardiomyocytes quickly and effectively.

Based on our experimental results, cells corrected at both alleles a1 and a2 have been modeled to secrete 3-fold more GAA than those edited at a single allele. Gene correction rates relative to other potential editing outcomes come from experiments with patient-derived fibroblasts. After delivery of the S1mplex genome editors, approximately 80-90% of all edits achieved gene correction. We utilize the nomenclature of Shen et al to describe this ratio of gene correction to other editing outcome. The remaining 10-20% of edits are imprecise at the on-target site, which could destroy the PAM or modify the on-target site for subsequent editing of these alleles, and these alleles are tracked in silico Tables 4-6 provide the forward and reverse primer sequences (Table 4), the off-target sequences and corresponding genomic locus for each sgRNA used (Table 5), and the forward and reverse primers used to amplify off-target genomic loci (Table 6).

TABLE 4

Forward and reverse primers for genomic loci.

| Name | Primer F (5'-3') | SEQ ID NO: | Primer R (5'-3') | SEQ ID NO: |
|---|---|---|---|---|
| 1441delT genomic | AGCTGCTCATTGACCTCCAG | 11 | CAATCCACATGCCGTCGAAG | 12 |
| 2237G>A genomic | AATTCAGCCTCTTCCTGTGC | 13 | CATACGTTCCTCTTTCCGCC | 14 |
| Full length genomic | TGACAGGTTTCCCTCTTCCCAG | 15 | TTGATAACCTACACTGCGGGGG | 16 |
| 1441delT qPCR/NGS | AGTGGGGCTTCCATGCAG | 17 | GGTTGGTGAAGTCGGGGAAG | 18 |
| 2237G>A qPCR/NGS | CCAAGGACTCTAGCACCTGGAC | 19 | GGGAAGTAGCCAGTCACTTCGG | 20 |
| W746X NGS | TCCCATTCATCACCCGTATGC | 66 | AGGTCGTACCATGTGCCCAA | 67 |
| D645N R660H NGS | CTGAGGACCAGCCTGACTCT | 68 | CCACCCTACCAGACTGAGCA | 69 |

TABLE 5

Off-target sequences and corresponding genomic locus for each sgRNA used. Mismatches from protospacer are bolded.

| sgRNA Target Sequence | Off-target sequence | SEQ ID NO: | Chromosome location |
|---|---|---|---|
| 2237G>A TGGACCACCAGCTCCTGTAG SEQ ID NO: 21 | OT1 TAGACCACCAGCTCCTGCAG | 22 | chr8:-42696136 |
| | OT2 CTCACCACCTGCTCCTGTAG | 23 | chr9:-123379574 |
| | OT3 TTGACCAGCAGCTCCTGTCG | 24 | chr15:-77699091 |
| 1441delT TGGACCACCAGCTCCTGTAG SEQ ID NO: 25 | OT1 CTGGTTGTCCAGGTGGGCCC | 26 | chr19:+9976610 |
| | OT2 CTCGATGGCCAGGTAGGCCT | 27 | chr9:+113788274 |
| | OT3 ATTATTGACCAGGTAGGCCC | 28 | chr20:-42195228 |

TABLE 6

Forward and reverse primers used to amplify off-target genomic loci.

| Off-Target Primer | Primer F (5'-3') | SEQ ID NO. | Primer R (5'-3') | SEQ ID NO: |
|---|---|---|---|---|
| 2237-OT1 | CCCTCCTCTGTGTGCCATTA | 29 | GTGCCATATTTTGGGGACCAC | 30 |
| 2237-OT2 | GGGGCATGGTCAGATGATGG | 31 | CACAGAAATTCCTGAGGCCAAC | 32 |
| 2237-OT3 | GGAGAGGCTGACCTTCATGG | 33 | TCGTGCTTTCCTGACCATCG | 34 |
| 1441-OT1 | AGTGTGCTTCCACTGTCGTT | 35 | GTGCGGGTAACCTTCTCCAT | 36 |
| 1441-OT2 | TTCCTCTGCTGCTGAGTTGG | 37 | GCCGATTAAAAGGCTGTCGC | 38 |
| 1441-OT3 | AGAGCCCTGGAGGTCATTGT | 39 | CTGTCTGGCCTCTGAATCGG | 40 |

DISCUSSION

While potential off-target effects and other safety concerns have been extensively studied, the efficacy of genome editing strategies has yet to be quantitatively analyzed, especially in polygenic cases. Emerging human cell based and in silico models have been used to facilitate translation of gene augmentation therapy, but have yet to be applied to genome editing. Our in vitro model constitutes a novel generalized framework to quantitatively understand the efficacy and potency of various genome editing strategies, and other gene and cell therapies.

We demonstrate biallelic gene correction with no detected off-target effects, and many of the common Pompe disease mutations can be targeted in an allele-specific manner using Sp.Cas9 strategies (Table 7). We observe that transcriptional regulation is driven by the endogenous promoter, potentially correcting a number of different isoforms for GAA. The targets for somatic cell genome editors therefore could expand from the traditional foci of liver and muscle to other tissues that may use alternate GAA isoforms. In contrast, in the gene augmentation approach, all cells must process a single isoform. Further, silencing from synthetic or viral elements has been observed for gene therapies, and in our hands with targeted knockin strategies that overexpress a transgene via a synthetic promoter. Transgene silencing raises concerns about the durability of viral gene therapies and proposed cell therapies where GAA is overexpressed from a safe harbor locus. In our strategy, post-translational processing of the enzyme also appears to be intact, as the distribution of processed GAA is identical to healthy controls. In contrast, GAA overexpression in mammalian cells can cause cellular stress, leading to differential trafficking and processing of the nascent translated peptide. The RNP-based correction strategy also avoids insertional oncogenesis by using a non-viral approach for delivery of the genome editor.

TABLE 7

Subset of mutations in GAA and accompanying allele-specific sgRNAs.
Bold denotes location of mutations relative to wildtype for allele-specific sgRNAs.
Italics denotes the PAM sequence.

| Mutation | sgRNA Sequence | SEQ ID NO: | Allele Frequency ($\times 10^{-5}$) |
|---|---|---|---|
| c.118C>T | GAGGAGCCACTCAGCTCTCA*GGG* | 41 | 0.86 |
| c.258dupC | ATCGAAGCGGCTGTTGGGGG*GGG* | 42 | 2.65 |
| c.525delT | CTGGACGTGATGATGGAGAC-*GAG* | 43 | 7.04 |
| c.1822C>T | AGTGGCCGGCGTATCAGCCG*TGG* | 44 | 2.76 |
| c.1827delC | TGCTGGCCACGGCCGATA-GCC*GG* | 45 | 3.75 |
| c.1930_1936dupGCCGACG | AAGCCGCAGACGTCGGCCGT*CGG* | 46 | 1.17 |
| c.2242dupG | CACCAGCTCCTGTAGGGGGGA*GG* | 47 | 1.66 |
| c.2.560C>T | ACCAAGGGTGGGGAGGCCTG*AGG* | 48 | 21.5 |
| c.2662G>T | TAACACGATCGTGAATTAGC*TGG* | 49 | 1.65 |

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A modified guide RNA, comprising
a crRNA comprising, a single-stranded protospacer sequence and a first complementary strand of a binding region for the Cas9 polypeptide, and
a tracrRNA comprising a second complementary strand of the binding region for the Cas9 polypeptide,
wherein the crRNA or the tracrRNA comprises an aptamer that binds an avidin molecule,
wherein the crRNA and the tracrRNA hybridize through the first and second complementary strands of the binding region for the Cas9 polypeptide,
wherein the single stranded protospacer region comprises

```
                                          (SEQ ID NO: 1)
CTCGTTGTCCAGGTAGGCCC, (SEQ ID NO: 2)
TGGACCACCAGCTCCTGTAG, (SEQ ID NO: 60)
GGACCACCAGCTCCTGTAGG, (SEQ ID NO: 61)
GCCCAGGAAGCCGCAGACGT,
or (SEQ ID NO: 62)
CAGAGGAGCTGTGTGTGCAC.
```

2. The modified guide RNA of claim 1, wherein the crRNA and the tracrRNA form an sgRNA, the sgRNA comprising, from 5' to 3',
the single-stranded protospacer sequence,
the first complementary strand of a binding region for the Cas9 polypeptide,
the aptamer that binds an avidin molecule, and
the second complementary strand of the binding region for the Cas9 polypeptide.

3. The modified guide RNA of claim 2, wherein, in the secondary structure of the modified sgRNA, the crRNA and the tracrRNA hybridize through the first and second complementary strands of the binding region for the Cas9 polypeptide and the aptamer that binds the avidin molecule form a stem-loop structure.

4. An RNP complex, comprising the modified guide RNA of claim 1, and a Cas9 polypeptide with nuclease activity.

5. A guide RNA, comprising
a crRNA comprising, a single-stranded protospacer sequence and a first complementary strand of a binding region for the Cas9 polypeptide, and
a tracrRNA comprising a second complementary strand of the binding region for the Cas9 polypeptide,
wherein the crRNA and the tracrRNA hybridize through the first and second complementary strands of the binding region for the Cas9 polypeptide,
wherein the single stranded protospacer region comprises

```
                                          (SEQ ID NO: 1)
CTCGTTGTCCAGGTAGGCCC, (SEQ ID NO: 2)
TGGACCACCAGCTCCTGTAG, (SEQ ID NO: 60)
GGACCACCAGCTCCTGTAGG,
```

```
                                          (SEQ ID NO: 61)
GCCCAGGAAGCCGCAGACGT,
or (SEQ ID NO: 62)
CAGAGGAGCTGTGTGTGCAC.
```

6. A method of modifying an acid-α-glucosidase (GAA) gene ex vivo in a patient-derived cell, wherein the patient has -Pompe disease, the method comprising
delivering to the cell a first modified guide RNA, a second modified guide RNA, a Cas9 polypeptide having nuclease activity, an avidin molecule, a first biotinylated donor polynucleotide, and a second biotinylated donor polynucleotide, wherein each modified guide RNA comprises,
a crRNA comprising, a single-stranded protospacer sequence and a first complementary strand of a binding region for the Cas9 polypeptide, and
a tracrRNA comprising a second complementary strand of the binding region for the Cas9 polypeptide,
wherein the crRNA or the tracrRNA comprises an aptamer that binds an avidin molecule,
wherein the crRNA and the tracrRNA hybridize through the first and second complementary strands of the binding region for the Cas9 polypeptide,
wherein the single-stranded protospacer sequence of the modified guide RNA hybridizes to a sequence in the GAA gene,
wherein the first modified guide RNA and the first biotinylated donor polynucleotide correct a first diseased allele,
wherein the second modified guide RNA and the second biotinylated donor polynucleotide correct a second diseased allele.

7. The method of claim 6, wherein the patient-derived cell comprises an induced pluripotent stem cell, a progenitor cell, a mesenchymal stem cell, or a tissue-specific stem cell.

8. The method of claim 7, wherein the tissue-specific stem cell comprises a skeletal stem cell, a hematopoietic stem cell, an epithelial stem cell, or a neural stem cell.

9. The method of claim 6, wherein a first RNP complex comprises the first modified guide RNA, the Cas9 polypeptide, the avidin molecule and the first biotinylated donor polynucleotide; and a second RNP complex comprises the second modified guide RNA, the Cas9 polypeptide, the avidin molecule and the second biotinylated donor polynucleotide.

10. The method of claim 6, wherein the first modified guide RNA, the second modified guide RNA and the Cas9 polypeptide are expressed from one or more viral vectors.

11. The method of claim 10, wherein a first viral vector expresses the first modified guide RNA, and a second viral vector expresses the second modified guide RNA, and a third viral vector expresses the Cas9 polypeptide.

12. The method of claim 6, wherein the wherein the avidin molecule is covalently linked to a donor polynucleotide, either directly or via a linker molecule.

13. The method of claim 6, wherein the biotinylated donor polynucleotide comprises a biotinylated nanoparticle, a dye, a contrast agent, a cell or tissue targeting ligand, or a peptide.

14. The method of claim 13, wherein the nanoparticle is a quantum dot, a gold particle, a magnetic particle, or a polymeric nanoparticle.

15. The method of claim 6, wherein the donor polynucleotide comprises single-stranded DNA, double-stranded DNA, RNA, or a duplex of RNA and DNA.

16. The method of claim 6, wherein the avidin molecule has one, two, three or four biotin binding sites, wherein the avidin molecule optionally comprises a fluorescent label.

17. A method of treating a patient with -Pompe disease, comprising transplanting the cell made by the method of claim 6 into the subject.

18. A method of modifying an acid-α-glucosidase (GAA) gene ex vivo in a patient-derived cell, wherein the patient has Pompe disease, the method comprising delivering to the cell a first modified guide RNA, a second modified guide RNA, a Cas9 polypeptide with nuclease activity, an avidin molecule, a first biotinylated donor polynucleotide, and a second biotinylated donor polynucleotide, wherein each modified guide RNA comprises, a crRNA comprising, a single-stranded protospacer sequence and a first complementary strand of a binding region for the Cas9 polypeptide, and a tracrRNA comprising a second complementary strand of the binding region for the Cas9 polypeptide, wherein the crRNA or the tracrRNA comprises an aptamer that binds an avidin molecule, wherein the crRNA and the tracrRNA hybridize through the first and second complementary strands of the binding region for the Cas9 polypeptide, wherein the single-stranded protospacer sequence of the modified guide RNA hybridizes to a sequence in the GAA gene, wherein the first modified guide RNA and the first biotinylated donor polynucleotide correct a first diseased allele, wherein the second modified guide RNA and the second biotinylated donor polynucleotide correct a second diseased allele, wherein the single stranded protospacer region of the first modified guide RNA comprises CTCGTTGTCCAGGTAGGCCC (SEQ ID NO: 1) and the single stranded protospacer region of the second guide RNA comprises TGGACCACCAGCTCCTGTA (SEQ ID NO: 2).

19. The method of claim 18, further comprising repeating the method and producing a second RNP complex, wherein the second RNP complex corrects a second mutant allele in the acid-α-glucosidase (GAA) gene expressed in Pompe disease to result in a biallelic correction.

20. A method of modifying an acid-α-glucosidase (GAA) in a patient-derived cell, wherein the patient has Pompe disease, the method comprising delivering to the cell a first guide RNA, a second guide RNA, a Cas9 polypeptide with nuclease activity, a first donor polynucleotide, and a second donor polynucleotide, wherein each guide RNA comprises, a crRNA comprising, a single-stranded protospacer sequence and a first complementary strand of a binding region for the Cas9 polypeptide, and a tracrRNA comprising a second complementary strand of the binding region for the Cas9 polypeptide, wherein the crRNA and the tracrRNA hybridize through the first and second complementary strands of the binding region for the Cas9 polypeptide, wherein the single-stranded protospacer sequence of the modified guide RNA hybridizes to a sequence in the GAA gene, wherein the first guide RNA and the first donor polynucleotide correct a first diseased allele, wherein the second guide RNA and the second donor polynucleotide correct a second diseased allele, wherein the single stranded protospacer region of the first modified guide RNA comprises CTCGTTGTCCAGGTAGGCCC (SEQ ID NO: 1) and the single stranded protospacer region of the second guide RNA comprises TGGACCACCAGCTCCTGTA (SEQ ID NO: 2).

21. A method of making an RNP complex, comprising selecting a single stranded protospacer sequence by identifying a mutant allele to be corrected, wherein the mutant allele is within 0 to 100 bases of a protospacer adjacent motif, wherein the mutant allele is in an acid-α-glucosidase (GAA) gene expressed in Pompe disease, producing a modified guide RNA comprising the selected single stranded protospacer region, wherein the modified guide RNA comprises a crRNA comprising the single-stranded protospacer sequence and a first complementary strand of a binding region for a Cas9 polypeptide with nuclease activity, and a tracrRNA comprising a second complementary strand of the binding region for the Cas9 polypeptide, wherein the crRNA or the tracrRNA comprises an aptamer that binds an avidin molecule, wherein the crRNA and the tracrRNA hybridize through the first and second complementary strands of the binding region for the Cas9 polypeptide, selecting a donor polynucleotide to correct the mutant allele and complementary to an anti-sense strand of genomic DNA, wherein the donor polynucleotide comprises a silent mutation in a constant region of the protospacer adjacent motif, producing a biotinylated donor polynucleotide, wherein the donor polynucleotide is biotinylated at the 5' end or the 3' end, and assembling the modified guide RNA, a Cas9 polypeptide, an avidin molecule, and the biotinylated donor polynucleotide.

* * * * *

SEQUENCE LISTING

```
<160> NUMBER OF SEQ ID NOS: 77

<210> SEQ ID NO 1
<211> LENGTH: 20
<212> TYPE: DNA
<213> ORGANISM: Artificial Sequence
<220> FEATURE:
<223> OTHER INFORMATION: protospacer region

<400> SEQUENCE: 1
ctcgttgtcc aggtaggccc                                              20

<210> SEQ ID NO 2
<211> LENGTH: 20
<212> TYPE: DNA
<213> ORGANISM: Artificial Sequence
<220> FEATURE:
<223> OTHER INFORMATION: protospacer region

<400> SEQUENCE: 2
tggaccacca gctcctgtag                                              20

<210> SEQ ID NO 3
<211> LENGTH: 1368
<212> TYPE: PRT
<213> ORGANISM: Streptococcus pyogenes

<400> SEQUENCE: 3

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95
```

```
Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
```

```
            515                 520                 525
Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940
```

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335
```

-continued

Thr Lys Glu Val Leu Asp Ala Thr Leu Ile His Gln Ser Ile Thr
   1340                1345                1350

Gly Leu Tyr Glu Thr Arg Ile Asp Leu Ser Gln Leu Gly Gly Asp
   1355                1360                1365

<210> SEQ ID NO 4
<211> LENGTH: 1409
<212> TYPE: PRT
<213> ORGANISM: Streptococcus thermophilus

<400> SEQUENCE: 4

Met Leu Phe Asn Lys Cys Ile Ile Ser Ile Asn Leu Asp Phe Ser
1                 5                  10                  15

Asn Lys Glu Lys Cys Met Thr Lys Pro Tyr Ser Ile Gly Leu Asp Ile
                  20                  25                  30

Gly Thr Asn Ser Val Gly Trp Ala Val Ile Thr Asp Asn Tyr Lys Val
              35                  40                  45

Pro Ser Lys Lys Met Lys Val Leu Gly Asn Thr Ser Lys Lys Tyr Ile
   50                  55                  60

Lys Lys Asn Leu Leu Gly Val Leu Leu Phe Asp Ser Gly Ile Thr Ala
65                  70                  75                  80

Glu Gly Arg Arg Leu Lys Arg Thr Ala Arg Arg Tyr Thr Arg Arg
                  85                  90                  95

Arg Asn Arg Ile Leu Tyr Leu Gln Glu Ile Phe Ser Thr Glu Met Ala
                  100                 105                 110

Thr Leu Asp Asp Ala Phe Phe Gln Arg Leu Asp Asp Ser Phe Leu Val
              115                 120                 125

Pro Asp Asp Lys Arg Asp Ser Lys Tyr Pro Ile Phe Gly Asn Leu Val
   130                 135                 140

Glu Glu Lys Val Tyr His Asp Glu Phe Pro Thr Ile Tyr His Leu Arg
145                 150                 155                 160

Lys Tyr Leu Ala Asp Ser Thr Lys Lys Ala Asp Leu Arg Leu Val Tyr
                  165                 170                 175

Leu Ala Leu Ala His Met Ile Lys Tyr Arg Gly His Phe Leu Ile Glu
              180                 185                 190

Gly Glu Phe Asn Ser Lys Asn Asn Asp Ile Gln Lys Asn Phe Gln Asp
   195                 200                 205

Phe Leu Asp Thr Tyr Asn Ala Ile Phe Glu Ser Asp Leu Ser Leu Glu
   210                 215                 220

Asn Ser Lys Gln Leu Glu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                  245                 250                 255

Gly Ile Phe Ser Glu Phe Leu Lys Leu Ile Val Gly Asn Gln Ala Asp
              260                 265                 270

Phe Arg Lys Cys Phe Asn Leu Asp Glu Lys Ala Ser Leu His Phe Ser
   275                 280                 285

Lys Glu Ser Tyr Asp Glu Asp Leu Glu Thr Leu Leu Gly Tyr Ile Gly
   290                 295                 300

Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
                  325                 330                 335

Pro Leu Ser Ser Ala Met Ile Lys Arg Tyr Asn Glu His Lys Glu Asp
              340                 345                 350

```
Leu Ala Leu Leu Lys Glu Tyr Ile Arg Asn Ile Ser Leu Lys Thr Tyr
            355                 360                 365

Asn Glu Val Phe Lys Asp Asp Thr Lys Asn Gly Tyr Ala Gly Tyr Ile
        370                 375                 380

Asp Gly Lys Thr Asn Gln Glu Asp Phe Tyr Val Tyr Leu Lys Asn Leu
385                 390                 395                 400

Leu Ala Glu Phe Glu Gly Ala Asp Tyr Phe Leu Glu Lys Ile Asp Arg
                405                 410                 415

Glu Asp Phe Leu Arg Lys Gln Arg Thr Phe Asp Asn Gly Ser Ile Pro
            420                 425                 430

Tyr Gln Ile His Leu Gln Glu Met Arg Ala Ile Leu Asp Lys Gln Ala
            435                 440                 445

Lys Phe Tyr Pro Phe Leu Ala Lys Asn Lys Glu Arg Ile Glu Lys Ile
        450                 455                 460

Leu Thr Phe Arg Ile Pro Tyr Tyr Val Gly Pro Leu Ala Arg Gly Asn
465                 470                 475                 480

Ser Asp Phe Ala Trp Ser Ile Arg Lys Arg Asn Glu Lys Ile Thr Pro
                485                 490                 495

Trp Asn Phe Glu Asp Val Ile Asp Lys Glu Ser Ser Ala Glu Ala Phe
            500                 505                 510

Ile Asn Arg Met Thr Ser Phe Asp Leu Tyr Leu Pro Glu Glu Lys Val
            515                 520                 525

Leu Pro Lys His Ser Leu Leu Tyr Glu Thr Phe Asn Val Tyr Asn Glu
        530                 535                 540

Leu Thr Lys Val Arg Phe Ile Ala Glu Ser Met Arg Asp Tyr Gln Phe
545                 550                 555                 560

Leu Asp Ser Lys Gln Lys Lys Asp Ile Val Arg Leu Tyr Phe Lys Asp
                565                 570                 575

Lys Arg Lys Val Thr Asp Lys Asp Ile Ile Glu Tyr Leu His Ala Ile
            580                 585                 590

Tyr Gly Tyr Asp Gly Ile Glu Leu Lys Gly Ile Glu Lys Gln Phe Asn
        595                 600                 605

Ser Ser Leu Ser Thr Tyr His Asp Leu Leu Asn Ile Ile Asn Asp Lys
        610                 615                 620

Glu Phe Leu Asp Asp Ser Ser Asn Glu Ala Ile Ile Glu Glu Ile Ile
625                 630                 635                 640

His Thr Leu Thr Ile Phe Glu Asp Arg Glu Met Ile Lys Gln Arg Leu
                645                 650                 655

Ser Lys Phe Glu Asn Ile Phe Asp Lys Ser Val Leu Lys Lys Leu Ser
            660                 665                 670

Arg Arg His Tyr Thr Gly Trp Gly Lys Leu Ser Ala Lys Leu Ile Asn
        675                 680                 685

Gly Ile Arg Asp Glu Lys Ser Gly Asn Thr Ile Leu Asp Tyr Leu Ile
        690                 695                 700

Asp Asp Gly Ile Ser Asn Arg Asn Phe Met Gln Leu Ile His Asp Asp
705                 710                 715                 720

Ala Leu Ser Phe Lys Lys Ile Gln Lys Ala Gln Ile Ile Gly Asp
                725                 730                 735

Glu Asp Lys Gly Asn Ile Lys Glu Val Val Lys Ser Leu Pro Gly Ser
            740                 745                 750

Pro Ala Ile Lys Lys Gly Ile Leu Gln Ser Ile Lys Ile Val Asp Glu
        755                 760                 765
```

-continued

Leu Val Lys Val Met Gly Gly Arg Lys Pro Glu Ser Ile Val Val Glu
770                 775                 780

Met Ala Arg Glu Asn Gln Tyr Thr Asn Gln Gly Lys Ser Asn Ser Gln
785                 790                 795                 800

Gln Arg Leu Lys Arg Leu Glu Lys Ser Leu Lys Glu Leu Gly Ser Lys
                805                 810                 815

Ile Leu Lys Glu Asn Ile Pro Ala Lys Leu Ser Lys Ile Asp Asn Asn
            820                 825                 830

Ala Leu Gln Asn Asp Arg Leu Tyr Leu Tyr Leu Gln Asn Gly Lys
                835                 840                 845

Asp Met Tyr Thr Gly Asp Asp Leu Asp Ile Asp Arg Leu Ser Asn Tyr
850                 855                 860

Asp Ile Asp His Ile Ile Pro Gln Ala Phe Leu Lys Asp Asn Ser Ile
865                 870                 875                 880

Asp Asn Lys Val Leu Val Ser Ser Ala Ser Asn Arg Gly Lys Ser Asp
                885                 890                 895

Asp Phe Pro Ser Leu Glu Val Val Lys Lys Arg Lys Thr Phe Trp Tyr
            900                 905                 910

Gln Leu Leu Lys Ser Lys Leu Ile Ser Gln Arg Lys Phe Asp Asn Leu
                915                 920                 925

Thr Lys Ala Glu Arg Gly Gly Leu Leu Pro Glu Asp Lys Ala Gly Phe
930                 935                 940

Ile Gln Arg Gln Leu Val Glu Thr Arg Gln Ile Thr Lys His Val Ala
945                 950                 955                 960

Arg Leu Leu Asp Glu Lys Phe Asn Asn Lys Lys Asp Glu Asn Arg
                965                 970                 975

Ala Val Arg Thr Val Lys Ile Ile Thr Leu Lys Ser Thr Leu Val Ser
            980                 985                 990

Gln Phe Arg Lys Asp Phe Glu Leu Tyr Lys Val Arg Glu Ile Asn Asp
                995                1000                1005

Phe His His Ala His Asp Ala Tyr Leu Asn Ala Val Ile Ala Ser
   1010                1015                1020

Ala Leu Leu Lys Lys Tyr Pro Lys Leu Glu Pro Glu Phe Val Tyr
   1025                1030                1035

Gly Asp Tyr Pro Lys Tyr Asn Ser Phe Arg Glu Arg Lys Ser Ala
   1040                1045                1050

Thr Glu Lys Val Tyr Phe Tyr Ser Asn Ile Met Asn Ile Phe Lys
   1055                1060                1065

Lys Ser Ile Ser Leu Ala Asp Gly Arg Val Ile Glu Arg Pro Leu
   1070                1075                1080

Ile Glu Val Asn Glu Glu Thr Gly Glu Ser Val Trp Asn Lys Glu
   1085                1090                1095

Ser Asp Leu Ala Thr Val Arg Arg Val Leu Ser Tyr Pro Gln Val
   1100                1105                1110

Asn Val Val Lys Lys Val Glu Glu Gln Asn His Gly Leu Asp Arg
   1115                1120                1125

Gly Lys Pro Lys Gly Leu Phe Asn Ala Asn Leu Ser Ser Lys Pro
   1130                1135                1140

Lys Pro Asn Ser Asn Glu Asn Leu Val Gly Ala Lys Glu Tyr Leu
   1145                1150                1155

Asp Pro Lys Lys Tyr Gly Gly Tyr Ala Gly Ile Ser Asn Ser Phe
   1160                1165                1170

Ala Val Leu Val Lys Gly Thr Ile Glu Lys Gly Ala Lys Lys Lys

```
            1175                1180                1185

Ile Thr Asn Val Leu Glu Phe Gln Gly Ile Ser Ile Leu Asp Arg
    1190                1195                1200

Ile Asn Tyr Arg Lys Asp Lys Leu Asn Phe Leu Leu Glu Lys Gly
    1205                1210                1215

Tyr Lys Asp Ile Glu Leu Ile Ile Glu Leu Pro Lys Tyr Ser Leu
    1220                1225                1230

Phe Glu Leu Ser Asp Gly Ser Arg Arg Met Leu Ala Ser Ile Leu
    1235                1240                1245

Ser Thr Asn Asn Lys Arg Gly Glu Ile His Lys Gly Asn Gln Ile
    1250                1255                1260

Phe Leu Ser Gln Lys Phe Val Lys Leu Leu Tyr His Ala Lys Arg
    1265                1270                1275

Ile Ser Asn Thr Ile Asn Glu Asn His Arg Lys Tyr Val Glu Asn
    1280                1285                1290

His Lys Lys Glu Phe Glu Glu Leu Phe Tyr Tyr Ile Leu Glu Phe
    1295                1300                1305

Asn Glu Asn Tyr Val Gly Ala Lys Lys Asn Gly Lys Leu Leu Asn
    1310                1315                1320

Ser Ala Phe Gln Ser Trp Gln Asn His Ser Ile Asp Glu Leu Cys
    1325                1330                1335

Ser Ser Phe Ile Gly Pro Thr Gly Ser Glu Arg Lys Gly Leu Phe
    1340                1345                1350

Glu Leu Thr Ser Arg Gly Ser Ala Ala Asp Phe Glu Phe Leu Gly
    1355                1360                1365

Val Lys Ile Pro Arg Tyr Arg Asp Tyr Thr Pro Ser Ser Leu Leu
    1370                1375                1380

Lys Asp Ala Thr Leu Ile His Gln Ser Val Thr Gly Leu Tyr Glu
    1385                1390                1395

Thr Arg Ile Asp Leu Ala Lys Leu Gly Glu Gly
    1400                1405

<210> SEQ ID NO 5
<211> LENGTH: 1082
<212> TYPE: PRT
<213> ORGANISM: Neisseria

<400> SEQUENCE: 5

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Glu
                20                  25                  30

Glu Asn Pro Ile Arg Leu Ile Asp Leu Gly Val Arg Val Phe Glu Arg
            35                  40                  45

Ala Glu Val Pro Lys Thr Gly Asp Ser Leu Ala Met Val Arg Arg Leu
        50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
                100                 105                 110

Leu Arg Ala Ala Ala Leu Asp Arg Lys Leu Thr Pro Leu Glu Trp Ser
            115                 120                 125
```

-continued

```
Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Ile Ser Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
```

```
                    545                 550                 555                 560

Gln Gln His Gly Lys Cys Leu Tyr Ser Gly Lys Glu Ile Asn Leu Gly
                                   565                 570                 575

Arg Leu Asn Glu Lys Gly Tyr Val Glu Ile Asp His Ala Leu Pro Phe
                                   580                 585                 590

Ser Arg Thr Trp Asp Asp Ser Phe Asn Asn Lys Val Leu Val Leu Gly
                                   595                 600                 605

Ser Glu Asn Gln Asn Lys Gly Asn Gln Thr Pro Tyr Glu Tyr Phe Asn
                                   610                 615                 620

Gly Lys Asp Asn Ser Arg Glu Trp Gln Glu Phe Lys Ala Arg Val Glu
               625                 630                 635                 640

Thr Ser Arg Phe Pro Arg Ser Lys Lys Gln Arg Ile Leu Leu Gln Lys
                                   645                 650                 655

Phe Asp Glu Asp Gly Phe Lys Glu Arg Asn Leu Asn Asp Thr Arg Tyr
                                   660                 665                 670

Val Asn Arg Phe Leu Cys Gln Phe Val Ala Asp Arg Met Arg Leu Thr
                                   675                 680                 685

Gly Lys Gly Lys Lys Arg Val Phe Ala Ser Asn Gly Gln Ile Thr Asn
                                   690                 695                 700

Leu Leu Arg Gly Phe Trp Gly Leu Arg Lys Val Arg Ala Glu Asn Asp
               705                 710                 715                 720

Arg His His Ala Leu Asp Ala Val Val Ala Cys Ser Thr Val Ala
                                   725                 730                 735

Met Gln Gln Lys Ile Thr Arg Phe Val Arg Tyr Lys Glu Met Asn Ala
                                   740                 745                 750

Phe Asp Gly Lys Thr Ile Asp Lys Glu Thr Gly Glu Val Leu His Gln
                                   755                 760                 765

Lys Thr His Phe Pro Gln Pro Trp Glu Phe Phe Ala Gln Glu Val Met
                                   770                 775                 780

Ile Arg Val Phe Gly Lys Pro Asp Gly Lys Pro Glu Phe Glu Glu Ala
               785                 790                 795                 800

Asp Thr Pro Glu Lys Leu Arg Thr Leu Leu Ala Glu Lys Leu Ser Ser
                                   805                 810                 815

Arg Pro Glu Ala Val His Glu Tyr Val Thr Pro Leu Phe Val Ser Arg
                                   820                 825                 830

Ala Pro Asn Arg Lys Met Ser Gly Gln Gly His Met Glu Thr Val Lys
                                   835                 840                 845

Ser Ala Lys Arg Leu Asp Glu Gly Val Ser Val Leu Arg Val Pro Leu
               850                 855                 860

Thr Gln Leu Lys Leu Lys Asp Leu Glu Lys Met Val Asn Arg Glu Arg
               865                 870                 875                 880

Glu Pro Lys Leu Tyr Glu Ala Leu Lys Ala Arg Leu Glu Ala His Lys
                                   885                 890                 895

Asp Asp Pro Ala Lys Ala Phe Ala Glu Pro Phe Tyr Lys Tyr Asp Lys
                                   900                 905                 910

Ala Gly Asn Arg Thr Gln Gln Val Lys Ala Val Arg Val Glu Gln Val
                                   915                 920                 925

Gln Lys Thr Gly Val Trp Val Arg Asn His Asn Gly Ile Ala Asp Asn
                                   930                 935                 940

Ala Thr Met Val Arg Val Asp Val Phe Glu Lys Gly Asp Lys Tyr Tyr
               945                 950                 955                 960

Leu Val Pro Ile Tyr Ser Trp Gln Val Ala Lys Gly Ile Leu Pro Asp
                                   965                 970                 975
```

```
Arg Ala Val Val Gln Gly Lys Asp Glu Glu Asp Trp Gln Leu Ile Asp
                980                 985                 990

Asp Ser Phe Asn Phe Lys Phe Ser Leu His Pro Asn Asp Leu Val Glu
            995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Pro Val Arg
    1070                1075                1080

<210> SEQ ID NO 6
<211> LENGTH: 1395
<212> TYPE: PRT
<213> ORGANISM: Treponema

<400> SEQUENCE: 6

Met Lys Lys Glu Ile Lys Asp Tyr Phe Leu Gly Leu Asp Val Gly Thr
1               5                   10                  15

Gly Ser Val Gly Trp Ala Val Thr Asp Thr Asp Tyr Lys Leu Leu Lys
                20                  25                  30

Ala Asn Arg Lys Asp Leu Trp Gly Met Arg Cys Phe Glu Thr Ala Glu
            35                  40                  45

Thr Ala Glu Val Arg Arg Leu His Arg Gly Ala Arg Arg Ile Glu
        50                  55                  60

Arg Arg Lys Lys Arg Ile Lys Leu Leu Gln Glu Leu Phe Ser Gln Glu
65                  70                  75                  80

Ile Ala Lys Thr Asp Glu Gly Phe Phe Gln Arg Met Lys Glu Ser Pro
                85                  90                  95

Phe Tyr Ala Glu Asp Lys Thr Ile Leu Gln Glu Asn Thr Leu Phe Asn
            100                 105                 110

Asp Lys Asp Phe Ala Asp Lys Thr Tyr His Lys Ala Tyr Pro Thr Ile
        115                 120                 125

Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175

Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Ile Leu Gly Leu Lys
    210                 215                 220

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Asp Phe Asp Ala Leu Ser
```

-continued

```
                260                 265                 270
Asp Asp Leu Ala Ser Ile Leu Gly Asp Ser Phe Glu Leu Leu Lys
            275                 280                 285

Ala Lys Ala Val Tyr Asn Cys Ser Val Leu Ser Lys Val Ile Gly Asp
        290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
                325                 330                 335

Asp Tyr Lys Lys Val Phe Gly Tyr Asn Lys Asn Glu Lys Asn Asn Asn
            340                 345                 350

Asn Tyr Ser Gly Tyr Val Gly Val Cys Lys Thr Lys Ser Lys Lys Leu
        355                 360                 365

Ile Ile Asn Asn Ser Val Asn Gln Glu Asp Phe Tyr Lys Phe Leu Lys
    370                 375                 380

Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
                405                 410                 415

Asn Ala Glu Ile Pro Tyr Gln Leu Arg Lys Met Glu Leu Glu Lys Ile
            420                 425                 430

Leu Ser Asn Ala Glu Lys His Phe Ser Phe Leu Lys Gln Lys Asp Glu
        435                 440                 445

Lys Gly Leu Ser His Ser Glu Lys Ile Ile Met Leu Leu Thr Phe Lys
450                 455                 460

Ile Pro Tyr Tyr Ile Gly Pro Ile Asn Asp Asn His Lys Lys Phe Phe
465                 470                 475                 480

Pro Asp Arg Cys Trp Val Val Lys Lys Glu Lys Ser Pro Ser Gly Lys
                485                 490                 495

Thr Thr Pro Trp Asn Phe Phe Asp His Ile Asp Lys Glu Lys Thr Ala
            500                 505                 510

Glu Ala Phe Ile Thr Ser Arg Thr Asn Phe Cys Thr Tyr Leu Val Gly
        515                 520                 525

Glu Ser Val Leu Pro Lys Ser Ser Leu Leu Tyr Ser Glu Tyr Thr Val
    530                 535                 540

Leu Asn Glu Ile Asn Asn Leu Gln Ile Ile Asp Gly Lys Asn Ile
545                 550                 555                 560

Cys Asp Ile Lys Leu Lys Gln Lys Ile Tyr Glu Asp Leu Phe Lys Lys
                565                 570                 575

Tyr Lys Lys Ile Thr Gln Lys Gln Ile Ser Thr Phe Ile Lys His Glu
            580                 585                 590

Gly Ile Cys Asn Lys Thr Asp Glu Val Ile Ile Leu Gly Ile Asp Lys
        595                 600                 605

Glu Cys Thr Ser Ser Leu Lys Ser Tyr Ile Glu Leu Lys Asn Ile Phe
    610                 615                 620

Gly Lys Gln Val Asp Glu Ile Ser Thr Lys Asn Met Leu Glu Glu Ile
625                 630                 635                 640

Ile Arg Trp Ala Thr Ile Tyr Asp Glu Gly Glu Gly Lys Thr Ile Leu
                645                 650                 655

Lys Thr Lys Ile Lys Ala Glu Tyr Gly Lys Tyr Cys Ser Asp Glu Gln
            660                 665                 670

Ile Lys Lys Ile Leu Asn Leu Lys Phe Ser Gly Trp Gly Arg Leu Ser
        675                 680                 685
```

-continued

Arg Lys Phe Leu Glu Thr Val Thr Ser Glu Met Pro Gly Phe Ser Glu
690                     695                 700

Pro Val Asn Ile Ile Thr Ala Met Arg Glu Thr Gln Asn Asn Leu Met
705                 710                 715                 720

Glu Leu Leu Ser Ser Glu Phe Thr Phe Thr Glu Asn Ile Lys Lys Ile
            725                 730                 735

Asn Ser Gly Phe Glu Asp Ala Glu Lys Gln Phe Ser Tyr Asp Gly Leu
            740                 745                 750

Val Lys Pro Leu Phe Leu Ser Pro Ser Val Lys Lys Met Leu Trp Gln
            755                 760                 765

Thr Leu Lys Leu Val Lys Glu Ile Ser His Ile Thr Gln Ala Pro Pro
770                 775                 780

Lys Lys Ile Phe Ile Glu Met Ala Lys Gly Ala Glu Leu Glu Pro Ala
785                 790                 795                 800

Arg Thr Lys Thr Arg Leu Lys Ile Leu Gln Asp Leu Tyr Asn Asn Cys
            805                 810                 815

Lys Asn Asp Ala Asp Ala Phe Ser Ser Glu Ile Lys Asp Leu Ser Gly
            820                 825                 830

Lys Ile Glu Asn Glu Asp Asn Leu Arg Leu Arg Ser Asp Lys Leu Tyr
            835                 840                 845

Leu Tyr Tyr Thr Gln Leu Gly Lys Cys Met Tyr Cys Gly Lys Pro Ile
850                 855                 860

Glu Ile Gly His Val Phe Asp Thr Ser Asn Tyr Asp Ile Asp His Ile
865                 870                 875                 880

Tyr Pro Gln Ser Lys Ile Lys Asp Asp Ser Ile Ser Asn Arg Val Leu
            885                 890                 895

Val Cys Ser Ser Cys Asn Lys Asn Lys Glu Asp Lys Tyr Pro Leu Lys
            900                 905                 910

Ser Glu Ile Gln Ser Lys Gln Arg Gly Phe Trp Asn Phe Leu Gln Arg
            915                 920                 925

Asn Asn Phe Ile Ser Leu Glu Lys Leu Asn Arg Leu Thr Arg Ala Thr
930                 935                 940

Pro Ile Ser Asp Asp Glu Thr Ala Lys Phe Ile Ala Arg Gln Leu Val
945                 950                 955                 960

Glu Thr Arg Gln Ala Thr Lys Val Ala Ala Lys Val Leu Glu Lys Met
            965                 970                 975

Phe Pro Glu Thr Lys Ile Val Tyr Ser Lys Ala Glu Thr Val Ser Met
            980                 985                 990

Phe Arg Asn Lys Phe Asp Ile Val Lys Cys Arg Glu Ile Asn Asp Phe
            995                 1000                1005

His His Ala His Asp Ala Tyr Leu Asn Ile Val Val Gly Asn Val
        1010                1015                1020

Tyr Asn Thr Lys Phe Thr Asn Pro Trp Asn Phe Ile Lys Glu
        1025                1030                1035

Lys Arg Asp Asn Pro Lys Ile Ala Asp Thr Tyr Asn Tyr Tyr Lys
        1040                1045                1050

Val Phe Asp Tyr Asp Val Lys Arg Asn Asn Ile Thr Ala Trp Glu
        1055                1060                1065

Lys Gly Lys Thr Ile Ile Thr Val Lys Asp Met Leu Lys Arg Asn
        1070                1075                1080

Thr Pro Ile Tyr Thr Arg Gln Ala Ala Cys Lys Lys Gly Glu Leu
        1085                1090                1095

```
Phe Asn Gln Thr Ile Met Lys Lys Gly Leu Gly Gln His Pro Leu
1100                1105                1110

Lys Lys Glu Gly Pro Phe Ser Asn Ile Ser Lys Tyr Gly Gly Tyr
1115                1120                1125

Asn Lys Val Ser Ala Ala Tyr Tyr Thr Leu Ile Glu Tyr Glu Glu
1130                1135                1140

Lys Gly Asn Lys Ile Arg Ser Leu Glu Thr Ile Pro Leu Tyr Leu
1145                1150                1155

Val Lys Asp Ile Gln Lys Asp Gln Asp Val Leu Lys Ser Tyr Leu
1160                1165                1170

Thr Asp Leu Leu Gly Lys Lys Glu Phe Lys Ile Leu Val Pro Lys
1175                1180                1185

Ile Lys Ile Asn Ser Leu Leu Lys Ile Asn Gly Phe Pro Cys His
1190                1195                1200

Ile Thr Gly Lys Thr Asn Asp Ser Phe Leu Leu Arg Pro Ala Val
1205                1210                1215

Gln Phe Cys Cys Ser Asn Asn Glu Val Leu Tyr Phe Lys Lys Ile
1220                1225                1230

Ile Arg Phe Ser Glu Ile Arg Ser Gln Arg Glu Lys Ile Gly Lys
1235                1240                1245

Thr Ile Ser Pro Tyr Glu Asp Leu Ser Phe Arg Ser Tyr Ile Lys
1250                1255                1260

Glu Asn Leu Trp Lys Lys Thr Lys Asn Asp Glu Ile Gly Glu Lys
1265                1270                1275

Glu Phe Tyr Asp Leu Leu Gln Lys Lys Asn Leu Glu Ile Tyr Asp
1280                1285                1290

Met Leu Leu Thr Lys His Lys Asp Thr Ile Tyr Lys Lys Arg Pro
1295                1300                1305

Asn Ser Ala Thr Ile Asp Ile Leu Val Lys Gly Lys Glu Lys Phe
1310                1315                1320

Lys Ser Leu Ile Ile Glu Asn Gln Phe Glu Val Ile Leu Glu Ile
1325                1330                1335

Leu Lys Leu Phe Ser Ala Thr Arg Asn Val Ser Asp Leu Gln His
1340                1345                1350

Ile Gly Gly Ser Lys Tyr Ser Gly Val Ala Lys Ile Gly Asn Lys
1355                1360                1365

Ile Ser Ser Leu Asp Asn Cys Ile Leu Ile Tyr Gln Ser Ile Thr
1370                1375                1380

Gly Ile Phe Glu Lys Arg Ile Asp Leu Leu Lys Val
1385                1390                1395

<210> SEQ ID NO 7
<211> LENGTH: 20
<212> TYPE: DNA
<213> ORGANISM: Artificial Sequence
<220> FEATURE:
<223> OTHER INFORMATION: protospacer

<400> SEQUENCE: 7
ctcgttgtcc aggtaggccc                                              20

<210> SEQ ID NO 8
<211> LENGTH: 20
<212> TYPE: DNA
<213> ORGANISM: Artificial Sequence
<220> FEATURE:
<223> OTHER INFORMATION: protospacer
```

```
<400> SEQUENCE: 8
tggaccacca gctcctgtag                                                   20

<210> SEQ ID NO 9
<211> LENGTH: 100
<212> TYPE: DNA
<213> ORGANISM: Artificial Sequence
<220> FEATURE:
<223> OTHER INFORMATION: ssODN

<400> SEQUENCE: 9
cttccatgca ggccctgggt ggggccgggt ctccccactg cagcctctcg ttgtccaggt       60
atggcccgga tccactgcct tccccgactt caccaacccc                            100

<210> SEQ ID NO 10
<211> LENGTH: 100
<212> TYPE: DNA
<213> ORGANISM: Artificial Sequence
<220> FEATURE:
<223> OTHER INFORMATION: ssODN

<400> SEQUENCE: 10
tgcccatccc ccttgcaggt tccccaagga ctctagcacc tggactgtgg accaccagct       60
cctgtgggga gaggccctgc tcatcacccc agtgctccag                            100

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
agctgctcat tgacctccag                                                   20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
caatccacat gccgtcgaag                                                   20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
aattcagcct cttcctgtgc                                                   20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
```
catacgttcc tctttccgcc                                                    20

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
tgacaggttt ccctcttccc ag                                                 22

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
ttgataacct acactgcggg gg                                                 22

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
agtggggctt ccatgcag                                                      18

<210> SEQ ID NO 18
<211> LENGTH: 20
<212> TYPE: DNA
<213> ORGANISM: Artificial Sequence
<220> FEATURE:
<223> OTHER INFORMATION: protein

<400> SEQUENCE: 18
ggttggtgaa gtcggggaag                                                    20

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
ccaaggactc tagcacctgg ac                                                 22

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
gggaagtagc cagtcacttc gg                                                 22

<210> SEQ ID NO 21
<211> LENGTH: 20
<212> TYPE: DNA
<213> ORGANISM: Artificial Sequence

```
<220> FEATURE:
<223> OTHER INFORMATION: sgRNA Target Sequence

<400> SEQUENCE: 21
tggaccacca gctcctgtag                                                   20

<210> SEQ ID NO 22
<211> LENGTH: 20
<212> TYPE: DNA
<213> ORGANISM: Artificial Sequence
<220> FEATURE:
<223> OTHER INFORMATION: Off-target sequence

<400> SEQUENCE: 22
tagaccacca gctcctgcag                                                   20

<210> SEQ ID NO 23
<211> LENGTH: 20
<212> TYPE: DNA
<213> ORGANISM: Artificial Sequence
<220> FEATURE:
<223> OTHER INFORMATION: Off-target sequence

<400> SEQUENCE: 23
ctcaccacct gctcctgtag                                                   20

<210> SEQ ID NO 24
<211> LENGTH: 20
<212> TYPE: DNA
<213> ORGANISM: Artificial Sequence
<220> FEATURE:
<223> OTHER INFORMATION: Off-target sequence

<400> SEQUENCE: 24
ttgaccagca gctcctgtcg                                                   20

<210> SEQ ID NO 25
<211> LENGTH: 20
<212> TYPE: DNA
<213> ORGANISM: Artificial Sequence
<220> FEATURE:
<223> OTHER INFORMATION: sgRNA Target Sequence

<400> SEQUENCE: 25
tggaccacca gctcctgtag                                                   20

<210> SEQ ID NO 26
<211> LENGTH: 20
<212> TYPE: DNA
<213> ORGANISM: Artificial Sequence
<220> FEATURE:
<223> OTHER INFORMATION: Off-target sequence

<400> SEQUENCE: 26
ctggttgtcc aggtgggccc                                                   20

<210> SEQ ID NO 27
<211> LENGTH: 20
<212> TYPE: DNA
<213> ORGANISM: Artificial Sequence
<220> FEATURE:
<223> OTHER INFORMATION: Off-target sequence

<400> SEQUENCE: 27
ctcgatggcc aggtaggcct                                                   20
```

```
<210> SEQ ID NO 28
<211> LENGTH: 20
<212> TYPE: DNA
<213> ORGANISM: Artificial Sequence
<220> FEATURE:
<223> OTHER INFORMATION: Off-target sequence

<400> SEQUENCE: 28
attattgacc aggtaggccc                                              20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
ccctcctctg tgtgccatta                                              20

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
gtgccatatt ttggggacca c                                            21

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
ggggcatggt cagatgatgg                                              20

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
cacagaaatt cctgaggcca ac                                           22

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ggagaggctg accttcatgg                                              20

<210> SEQ ID NO 34
<211> LENGTH: 20
<212> TYPE: DNA
<213> ORGANISM: Artificial Sequence
<220> FEATURE:
<223> OTHER INFORMATION: primer
```

-continued

```
<400> SEQUENCE: 34
tcgtgctttc ctgaccatcg                                               20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
agtgtgcttc cactgtcgtt                                               20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
gtgcgggtaa ccttctccat                                               20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
ttcctctgct gctgagttgg                                               20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
gccgattaaa aggctgtcgc                                               20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
agagccctgg aggtcattgt                                               20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
ctgtctggcc tctgaatcgg                                               20

<210> SEQ ID NO 41
```

```
<211> LENGTH: 23
<212> TYPE: DNA
<213> ORGANISM: Artificial Sequence
<220> FEATURE:
<223> OTHER INFORMATION: sgRNA sequence

<400> SEQUENCE: 41
gaggagccac tcagctctca ggg                                          23

<210> SEQ ID NO 42
<211> LENGTH: 23
<212> TYPE: DNA
<213> ORGANISM: Artificial Sequence
<220> FEATURE:
<223> OTHER INFORMATION: sgRNA sequence

<400> SEQUENCE: 42
atcgaagcgg ctgttggggg ggg                                          23

<210> SEQ ID NO 43
<211> LENGTH: 23
<212> TYPE: DNA
<213> ORGANISM: Artificial Sequence
<220> FEATURE:
<223> OTHER INFORMATION: sgRNA sequence

<400> SEQUENCE: 43
ctggacgtga tgatggagac gag                                          23

<210> SEQ ID NO 44
<211> LENGTH: 23
<212> TYPE: DNA
<213> ORGANISM: Artificial Sequence
<220> FEATURE:
<223> OTHER INFORMATION: sgRNA sequence

<400> SEQUENCE: 44
agtggccggc gtatcagccg tgg                                          23

<210> SEQ ID NO 45
<211> LENGTH: 23
<212> TYPE: DNA
<213> ORGANISM: Artificial Sequence
<220> FEATURE:
<223> OTHER INFORMATION: sgRNA sequence

<400> SEQUENCE: 45
tgctggccac ggccgatagc cgg                                          23

<210> SEQ ID NO 46
<211> LENGTH: 23
<212> TYPE: DNA
<213> ORGANISM: Artificial Sequence
<220> FEATURE:
<223> OTHER INFORMATION: sgRNA sequence

<400> SEQUENCE: 46
aagccgcaga cgtcggccgt cgg                                          23

<210> SEQ ID NO 47
<211> LENGTH: 23
<212> TYPE: DNA
<213> ORGANISM: Artificial Sequence
<220> FEATURE:
<223> OTHER INFORMATION: sgRNA sequence

<400> SEQUENCE: 47
```
caccagctcc tgtagggggg agg          23

<210> SEQ ID NO 48
<211> LENGTH: 23
<212> TYPE: DNA
<213> ORGANISM: Artificial Sequence
<220> FEATURE:
<223> OTHER INFORMATION: sgRNA sequence

<400> SEQUENCE: 48
accaagggtg gggaggcctg agg          23

<210> SEQ ID NO 49
<211> LENGTH: 23
<212> TYPE: DNA
<213> ORGANISM: Artificial Sequence
<220> FEATURE:
<223> OTHER INFORMATION: sgRNA sequence

<400> SEQUENCE: 49
taacacgatc gtgaattagc tgg          23

<210> SEQ ID NO 50
<211> LENGTH: 30
<212> TYPE: DNA
<213> ORGANISM: Artificial Sequence
<220> FEATURE:
<223> OTHER INFORMATION: 2237G repair ssODN

<400> SEQUENCE: 50
gactgtggac caccagctcc tgtggggaga          30

<210> SEQ ID NO 51
<211> LENGTH: 30
<212> TYPE: DNA
<213> ORGANISM: Artificial Sequence
<220> FEATURE:
<223> OTHER INFORMATION: allele 1

<400> SEQUENCE: 51
gactgtggac caccagctcc tgtagggaga          30

<210> SEQ ID NO 52
<211> LENGTH: 30
<212> TYPE: DNA
<213> ORGANISM: Artificial Sequence
<220> FEATURE:
<223> OTHER INFORMATION: allele 2

<400> SEQUENCE: 52
gactgtggac caccagctcc tgtgggggga          30

<210> SEQ ID NO 53
<211> LENGTH: 33
<212> TYPE: DNA
<213> ORGANISM: Artificial Sequence
<220> FEATURE:
<223> OTHER INFORMATION: 1441 insT repair ssODN

<400> SEQUENCE: 53
gcctctcgtt gtccaggtat ggcccggatc cac          33

<210> SEQ ID NO 54
<211> LENGTH: 33
<212> TYPE: DNA

```
<213> ORGANISM: Artificial Sequence
<220> FEATURE:
<223> OTHER INFORMATION: allele 2

<400> SEQUENCE: 54
gcctctcgtt gtccaggtat ggcccgggtc cac                                33

<210> SEQ ID NO 55
<211> LENGTH: 33
<212> TYPE: DNA
<213> ORGANISM: Artificial Sequence
<220> FEATURE:
<223> OTHER INFORMATION: allele 1

<400> SEQUENCE: 55
gcctctcgtt gtccaggtat ggcccgggtc cac                                33

<210> SEQ ID NO 56
<211> LENGTH: 30
<212> TYPE: DNA
<213> ORGANISM: Artificial Sequence
<220> FEATURE:
<223> OTHER INFORMATION: unedited allele
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 56
gcctctcgtt gtccaggtan gnccnggntc                                    30

<210> SEQ ID NO 57
<211> LENGTH: 30
<212> TYPE: DNA
<213> ORGANISM: Artificial Sequence
<220> FEATURE:
<223> OTHER INFORMATION: 1441 delT corrected

<400> SEQUENCE: 57
gcctctcgtt gtccaggtat ggcccggatc                                    30

<210> SEQ ID NO 58
<211> LENGTH: 28
<212> TYPE: DNA
<213> ORGANISM: Artificial Sequence
<220> FEATURE:
<223> OTHER INFORMATION: unedited allele
<220> FEATURE:
<221> NAME/KEY: misc_feature
<222> LOCATION: (24)..(24)
<223> OTHER INFORMATION: n is a, c, g, or t

<400> SEQUENCE: 58
gactgtggac caccagctcc tgtngggg                                      28

<210> SEQ ID NO 59
<211> LENGTH: 28
```

```
<212> TYPE: DNA
<213> ORGANISM: Artificial Sequence
<220> FEATURE:
<223> OTHER INFORMATION: 2337G>A corrected

<400> SEQUENCE: 59
gactgtggac caccagctcc tgtgggag                                          28

<210> SEQ ID NO 60
<211> LENGTH: 20
<212> TYPE: DNA
<213> ORGANISM: Artificial Sequence
<220> FEATURE:
<223> OTHER INFORMATION: protospacer

<400> SEQUENCE: 60
ggaccaccag ctcctgtagg                                                   20

<210> SEQ ID NO 61
<211> LENGTH: 20
<212> TYPE: DNA
<213> ORGANISM: Artificial Sequence
<220> FEATURE:
<223> OTHER INFORMATION: protospacer

<400> SEQUENCE: 61
gcccaggaag ccgcagacgt                                                   20

<210> SEQ ID NO 62
<211> LENGTH: 20
<212> TYPE: DNA
<213> ORGANISM: Artificial Sequence
<220> FEATURE:
<223> OTHER INFORMATION: Protospacer

<400> SEQUENCE: 62
cagaggagct gtgtgtgcac                                                   20

<210> SEQ ID NO 63
<211> LENGTH: 100
<212> TYPE: DNA
<213> ORGANISM: Artificial Sequence
<220> FEATURE:
<223> OTHER INFORMATION: ssODN

<400> SEQUENCE: 63
tgcccatccc ccttgcaggt tccccaagga ctctagcacc tggactgtgg accaccagct       60
cctgtgggga gaggccctgc tcatcacccc agtgctccag                            100

<210> SEQ ID NO 64
<211> LENGTH: 100
<212> TYPE: DNA
<213> ORGANISM: Artificial Sequence
<220> FEATURE:
<223> OTHER INFORMATION: ssODN

<400> SEQUENCE: 64
agaaatcctg cagtttaacc tgctgggggt gcctctggtc ggggcagacg tctgtggctt       60
cctgggcaac acctcagagg agctgtgtgt gcactggacc                            100

<210> SEQ ID NO 65
<211> LENGTH: 100
<212> TYPE: DNA
<213> ORGANISM: Artificial Sequence
<220> FEATURE:
```

<223> OTHER INFORMATION: ssODN

<400> SEQUENCE: 65
gggccaacgt ctgcggcttc ctgggcaaca cctcagagga gctatgtgtg cgctggaccc    60
agctgggggc cttctacccc ttcatgcgga accacaacag    100

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
tcccattcat cacccgtatg c    21

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
aggtcgtacc atgtgcccaa    20

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
ctgaggacca gcctgactct    20

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
ccaccctacc agactgagca    20

<210> SEQ ID NO 70
<211> LENGTH: 33
<212> TYPE: DNA
<213> ORGANISM: Artificial Sequence
<220> FEATURE:
<223> OTHER INFORMATION: Unedited sequence, 1441delT corrected
<220> FEATURE:
<221> NAME/KEY: misc_feature
<222> LOCATION: (24)..(24)
<223> OTHER INFORMATION: n is a, c, g, or t

<400> SEQUENCE: 70
gactgtggac caccagctcc tgtnggggg agg    33

<210> SEQ ID NO 71
<211> LENGTH: 32
<212> TYPE: DNA
<213> ORGANISM: Artificial Sequence
<220> FEATURE:
<223> OTHER INFORMATION: 2237G>A corrected, double corrected

```
<400> SEQUENCE: 71
gactgtggac caccagctcc tgtggggaga gg                                    32

<210> SEQ ID NO 72
<211> LENGTH: 40
<212> TYPE: DNA
<213> ORGANISM: Artificial Sequence
<220> FEATURE:
<223> OTHER INFORMATION: 2237 OT-1

<400> SEQUENCE: 72
cctcccttcc tagaccacca gctcctgcag gagggcttgg                            40

<210> SEQ ID NO 73
<211> LENGTH: 40
<212> TYPE: DNA
<213> ORGANISM: Artificial Sequence
<220> FEATURE:
<223> OTHER INFORMATION: 2237 OT-2

<400> SEQUENCE: 73
gcccctgcct ctacaggagc aggtggtgag gatggctccg                            40

<210> SEQ ID NO 74
<211> LENGTH: 40
<212> TYPE: DNA
<213> ORGANISM: Artificial Sequence
<220> FEATURE:
<223> OTHER INFORMATION: 2237 OT-3

<400> SEQUENCE: 74
cacgctgcca cgacaggagc tgctggtcaa ctcctcctct                            40

<210> SEQ ID NO 75
<211> LENGTH: 40
<212> TYPE: DNA
<213> ORGANISM: Artificial Sequence
<220> FEATURE:
<223> OTHER INFORMATION: 1441 OT-1

<400> SEQUENCE: 75
ccccgtatcc ctggttgtcc aggtgggccc tgggagaaca                            40

<210> SEQ ID NO 76
<211> LENGTH: 40
<212> TYPE: DNA
<213> ORGANISM: Artificial Sequence
<220> FEATURE:
<223> OTHER INFORMATION: 1441 OT-2

<400> SEQUENCE: 76
cagctgccgt ctcgatggcc aggtaggcct gggcaaggac                            40

<210> SEQ ID NO 77
<211> LENGTH: 40
<212> TYPE: DNA
<213> ORGANISM: Artificial Sequence
<220> FEATURE:
<223> OTHER INFORMATION: 1441 OT-3

<400> SEQUENCE: 77
aattaggcta gggcctacct ggtcaataat gaaataattg                            40
```